(12) United States Patent
Adams

(10) Patent No.: US 7,131,975 B2
(45) Date of Patent: Nov. 7, 2006

(54) APPARATUS AND METHODS FOR STRAIGHTENING ANGLED TISSUE CUTTING INSTRUMENTS

(75) Inventor: Kenneth Adams, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 495 days.

(21) Appl. No.: 10/244,062

(22) Filed: Sep. 16, 2002

(65) Prior Publication Data

US 2004/0127927 A1   Jul. 1, 2004

(51) Int. Cl.
*A61F 2/38* (2006.01)

(52) U.S. Cl. .................. 606/101; 606/104; 81/489; 72/457; 72/479

(58) Field of Classification Search .......... 606/101, 606/104, 167; 81/489, 491, 487; 72/457, 72/479
See application file for complete search history.

(56) References Cited

U.S. PATENT DOCUMENTS

| 177,490 | A |   | 5/1876 | Fones et al. |
|---|---|---|---|---|
| 2,824,475 | A | * | 2/1958 | Rolando .................. 72/457 |
| 3,722,256 | A | * | 3/1973 | Iascone .................. 72/470 |
| 4,387,479 | A | * | 6/1983 | Kigyos .................. 15/167.1 |
| 4,416,143 | A | * | 11/1983 | Fouroux et al. ............ 72/479 |
| 4,446,429 | A |   | 5/1984 | Loscher et al. |
| 4,646,738 | A |   | 3/1987 | Trott |
| 5,152,744 | A |   | 10/1992 | Krause et al. |
| 5,161,404 | A | * | 11/1992 | Hayes .................. 72/458 |
| 5,201,210 | A | * | 4/1993 | Stein, III .................. 72/457 |
| 5,286,253 | A |   | 2/1994 | Fucci |
| 5,313,684 | A | * | 5/1994 | Fitjer .................. 15/167.1 |
| 5,322,505 | A |   | 6/1994 | Krause et al. |
| 5,411,514 | A |   | 5/1995 | Fucci et al. |
| 5,437,630 | A |   | 8/1995 | Daniel et al. |
| 5,529,580 | A |   | 6/1996 | Kusunoki et al. |
| 5,601,506 | A |   | 2/1997 | Long et al. |
| 5,601,586 | A |   | 2/1997 | Fucci et al. |
| 5,620,415 | A |   | 4/1997 | Lucey et al. |

(Continued)

OTHER PUBLICATIONS

Medtronic Xomed Product Spotlight, "RAD® Curved Blades", Jul. 24, 2002, 3 pgs.

(Continued)

*Primary Examiner*—Anhtuan T. Nguyen
*Assistant Examiner*—Michael G Mendoza

(57) ABSTRACT

A straightening tool is disclosed for straightening angled tissue cutting instruments including an outer member having a proximal length portion and a pre-formed bend connecting the proximal length portion with a distal length portion extending from the bend at an angle to a distal end, and a flexible inner member movably disposed in the outer member to cut anatomical tissue. The straightening tool comprises a handle and a positioning block extending from the handle coaxial with the straightening tool. The positioning block has a longitudinal bore for receiving the distal length portion therethrough to position the distal end within a cavity of the positioning block and the bend within a longitudinal slot of the positioning block with the proximal length portion extending externally through an opening of the slot. The bore confines the distal length portion against radial movement and serves as a fulcrum about which the proximal length portion is manually pivotable into abutment with a floor of the slot extending from the bore at an angle in a direction opposite the slot opening. Upon release of the manual pivoting force, the proximal length portion springs back somewhat in the direction of the original bend to obtain a longitudinally straightened outer member. The straightened outer member is used with the inner member to cut anatomical tissue as a straightened tissue cutting instrument.

58 Claims, 9 Drawing Sheets

U.S. PATENT DOCUMENTS

| | | |
|---|---|---|
| 5,620,447 A | 4/1997 | Smith et al. |
| 5,782,795 A | 7/1998 | Bays |
| 5,916,231 A | 6/1999 | Bays |
| 5,922,003 A | 7/1999 | Anctil et al. |
| 5,957,881 A | 9/1999 | Peters et al. |
| 6,010,477 A | 1/2000 | Bays |
| 6,183,433 B1 | 2/2001 | Bays |
| 6,293,957 B1 | 9/2001 | Peters et al. |
| 6,312,438 B1 | 11/2001 | Adams |
| 6,634,392 B1 * | 10/2003 | Breen .................. 140/147 |

OTHER PUBLICATIONS

Medtronic Xomed Surgical Techniques, Powered Adenoidectomy Using the RADenoid® Blade, Jul. 24, 2002, 3 pgs.

* cited by examiner

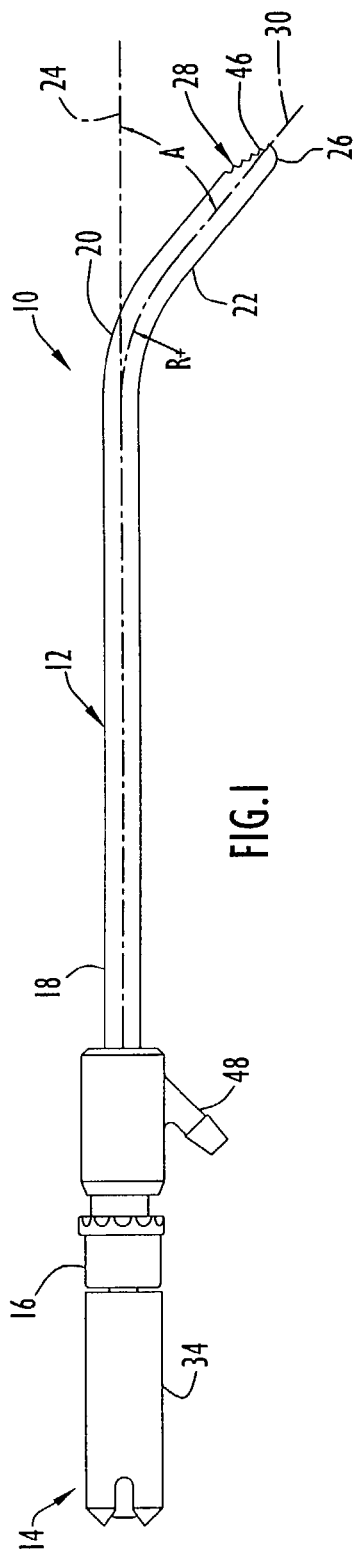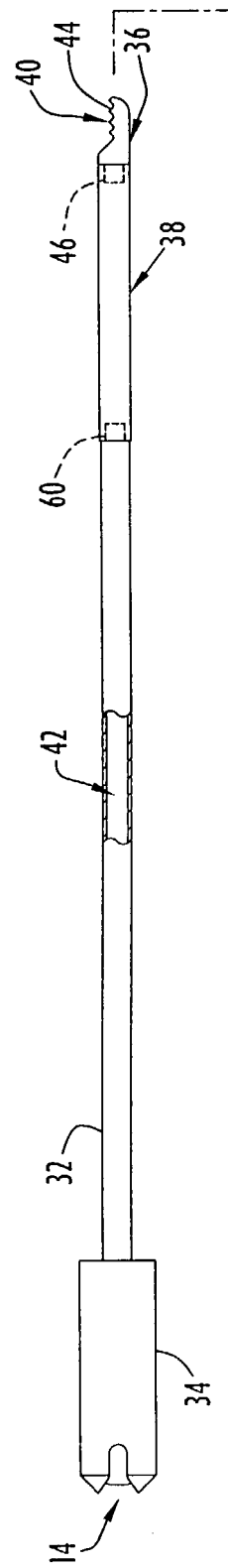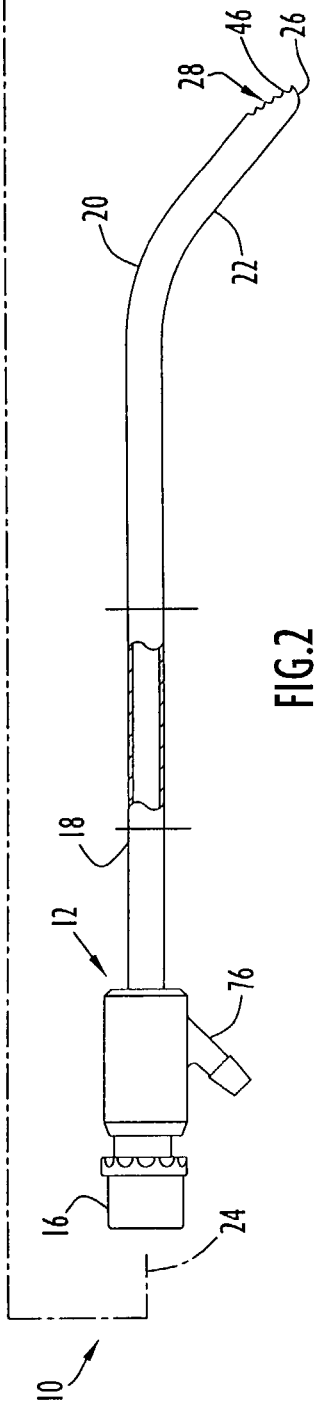
FIG.1
FIG.2

APPARATUS AND METHODS FOR STRAIGHTENING ANGLED TISSUE CUTTING INSTRUMENTS

BACKGROUND OF THE INVENTION

1. Field of the Invention

The present invention relates generally to angled tissue cutting instruments having pre-formed bends and, more particularly, to apparatus and methods for straightening the pre-formed bends of angled tissue cutting instruments.

2. Brief Discussion of the Related Art

Tissue cutting instruments comprising an elongate outer tubular member and an elongate inner member rotatably disposed in the outer tubular member to cut anatomical tissue have become well accepted for use in various surgical procedures. Typically, the inner member has a distal end with a cutting edge and the outer member has an opening through which the cutting edge is exposed to access anatomical tissue to be cut by the cutting edge when the inner member is rotated within the outer member. The cutting edge may have various configurations in accordance with the type of tissue and/or the type of cutting action to be accomplished. In some instances, the distal end of the outer member has a cutting edge cooperable with the cutting edge of the inner member to cut the anatomical tissue as the inner member is rotated. The outer and inner members ordinarily have proximal ends adapted for coupling with a powered surgical handpiece used to rotate the inner member relative to and within the outer member. Many tissue cutting instruments provide for aspiration of anatomical debris through the tissue cutting instrument and/or irrigation at the operative site via an irrigating or flushing fluid supplied along the tissue cutting instrument.

In tissue cutting instruments of the foregoing type, the outer members may be longitudinally or axially straight or may be longitudinally or axially bent, angled or curved depending on the surgical procedure being performed. Where the outer members are longitudinally or axially bent, angled or curved, the inner members are normally provided with a flexible region adjacent the bend, angle or curve in the outer member whereby the inner member assumes the longitudinally or axially bent, angled or curved configuration of the outer member while still being rotatable within the outer member. Angled tissue cutting instruments of the latter type are represented by U.S. Pat. No. 177,490 to Fones, No. 4,445,509 to Auth, No. 4,466,429 to Loscher, No. 4,646,738 to Trott, No. 5,152,744 and No. 5,322,505 to Krause et al, No. 5,286,253, No. 5,411,514 and No. 5,601,586 to Fucci et al, No. 5,437,630 to Daniel et al, No. 5,529,580 to Kusumoki et al, No. 5,620,415 to Lucy et al, and No. 5,620,447 to Smith et al. In most angled tissue cutting instruments, the bend, curve or angle is pre-formed in the outer member as part of the manufacturing or fabrication process and is essentially rigid or fixed. However, U.S. Pat. No. 5,601,586 and No. 5,411,514 to Fucci et al are representative of variable angle tissue cutting instruments in which a longitudinally straight outer member has a spiral relief cut forming a non-rigid bendable section along which the outer member may be bent axially by a user, and the inner member is flexible to follow the bent configuration of the outer member. The Fucci et al patents also disclose a bending tool permitting a user to bend the longitudinally straight outer member axially along the non-rigid bendable section to assume various predetermined angles.

Angled tissue cutting instruments comprising essentially rigid outer members having pre-formed angles, bends or curves and rotatable inner members following the pre-formed configurations of the outer members are illustrated by U.S. Pat. No. 5,922,003 to Anctil et al. Outer members that are pre-formed with a longitudinal or axial bend, angle or curve may advantageously be precision manufactured with the bend, angle or curve formed with exactitude to extend in a pre-selected direction at a specified location and angle with a predetermined radius of curvature. Accordingly, the outer member can be manufactured with a pre-formed angle, bend or curve that is optimal for the surgical procedure being performed. As an example, the Anctil et al patent discloses an angled tissue cutting instrument in which the outer member has a pre-formed bend, curve or angle that is optimal for use of the instrument as an adenoid blade. In many surgical procedures facilitated by an angled tissue cutting instrument, it is preferable that the outer member be pre-formed with the most desirable or advantageous bend, curve or angle for the particular surgical procedure to ensure that the most optimal outer member configuration is used for the particular surgical procedure.

In some surgical procedures, it is desirable to utilize angled tissue cutting instruments to remove anatomical tissue and to thereafter utilize longitudinally or axially straight tissue cutting instruments for further removal of anatomical tissue. In a combined tonsillectomy and adenoidectomy procedure (T&A procedure), for instance, an adenoidectomy is performed prior to a tonsillectomy to remove all or part of an adenoid using an angled tissue cutting instrument as represented by the adenoid blade disclosed in the Anctil et al patent and by the RADenoid® Blade of Medtronic Xomed Surgical Products, Inc. The tonsillectomy is thereafter performed, typically utilizing the same angled tissue cutting instrument or another different tissue cutting instrument in which the outer member is longitudinally or axially straight. Performing the tonsillectomy using the angled tissue cutting instrument that was used for the adenoidectomy, i.e. the adenoid blade, is disadvantageous since longitudinally or axially straight tissue cutting instruments provide better access to the tonsils. Using another different tissue cutting instrument having a longitudinally or axially straight outer member for the tonsillectomy is also disadvantageous for the increased cost associated with an additional instrument and/or the additional surgical time associated with preparing the additional instrument for use. The added steps involved in preparing an additional instrument for use during surgery may include removing the instrument from its package, assembling the inner member of the instrument within the outer member, coupling the inner member and the outer member to the surgical handpiece, and/or removing the angled tissue cutting instrument from the surgical handpiece so that the same handpiece can be coupled with the inner and outer members of the additional instrument. Furthermore, the need to inventory and supply both angled and straight tissue cutting instruments for a surgical procedure imposes a difficult burden on hospitals and other surgical sites.

In various sinus procedures, it is also common for surgeons to initially utilize an angled tissue cutting instrument to remove anatomical tissue and to thereafter utilize a straight tissue cutting instrument to further remove anatomical tissue. The Rad® 40 Curved Blade and the Rad 60 X-TREME™ Curved Blade of Medtronic Xomed Surgical Products are representative of angled tissue cutting instruments which allow access into the frontal recess and maxillary sinus and are popular for use in sinus surgery, particularly superior ethmoid and frontal recess surgery, removal of maxillary polyps, uncinectomy and antrostomy.

During sinus surgery where tissue removal is initially effected using an angled tissue cutting instrument, the surgeon will sometimes switch to a longitudinally straight tissue cutting instrument where needed to afford better access for further tissue removal. As discussed above, the need to switch between two different instruments during a surgical procedure presents numerous drawbacks.

Sometimes angled tissue cutting instruments having blades with a particular distal end cutting configuration are available to surgeons without there being available straight tissue cutting instruments having the particular distal end cutting configuration. There arises an unsatisfied need where a surgeon desires to use the particular distal end cutting configuration of an available angled tissue cutting instrument but as a longitudinally straight tissue cutting instrument. Accordingly, an angled tissue cutting instrument may have to be used in a surgical procedure in which use of a counterpart straight tissue cutting instrument would be more preferable.

It is seen from the above that a need exists for apparatus and methods to effect unbending or straightening of a pre-formed angle, bend or curve in an outer member of an angled tissue cutting instrument to obtain a longitudinally or axially straightened tissue cutting instrument therefrom. Apparatus and methods are needed which are capable of accomplishing unbending or straightening of an angled tissue cutting instrument prior to or during a surgical procedure in a brief amount of time using a minimal number of simple procedural steps. In particular, apparatus and methods are needed for unbending or straightening an angled tissue cutting instrument for use as a longitudinally straightened tissue cutting instrument during a surgical procedure to ensure that the instrument has both the optimal distal end cutting configuration and the optimal longitudinal configuration for the surgical procedure and/or to eliminate the need for surgeons to switch between different instruments during the surgical procedure. There is also a need to reduce the number of different instruments made available for and/or used during a surgical procedure to reduce surgical costs and the burden on hospitals and other surgical sites associated with maintaining and supplying many different instruments. Especially in the areas of T&A procedures and sinus procedures, the need exists for allowing a pre-formed angled tissue cutting instrument to be used in a surgical procedure to remove anatomical tissue and to be thereafter straightened or unbent for further use in the surgical procedure to remove anatomical tissue as a longitudinally straightened tissue cutting instrument. There is also a need to permit an available angled tissue cutting instrument having a particular distal end cutting configuration desirable for use in a surgical procedure to be straightened or unbent prior to the surgical procedure to assume a straightened longitudinal configuration that is more preferable for the surgical procedure than an angled configuration.

SUMMARY OF THE INVENTION

Accordingly, it is a primary object of the present invention to overcome the aforementioned disadvantages of the prior art.

Another object of the present invention is to straighten a pre-bent adenoid blade subsequent to performing an adenoidectomy with the adenoid blade and to thereafter perform a tonsillectomy with the straightened blade.

A further object of the present invention is to eliminate the need for hospitals and other surgical sites to supply both angled and straight tissue cutting instruments for T&A, sinus, laryngeal and other surgical procedures.

The present invention also has as an object to ensure the use of the most optimal distal end cutting configurations and/or longitudinal configurations for a blade used throughout a surgical procedure such as T&A, sinus, laryngeal and other surgical procedures.

An additional object of the present invention is to straighten a pre-bent angled tissue cutting instrument used during a surgical procedure for subsequent use during the surgical procedure as a longitudinally straightened tissue cutting instrument.

Still a further object of the present invention is to straighten an available angled tissue cutting instrument prior to a surgical procedure to obtain a straightened tissue cutting instrument that is more preferable for use in the surgical procedure than the angled instrument.

It is also an object of the present invention to utilize one tissue cutting instrument in a surgical procedure normally requiring a plurality of different tissue cutting instruments.

The present invention has as another object to reduce the cost of surgery by reducing the number of different tissue cutting instruments required to perform a surgical procedure.

Yet a further object of the present invention is to reduce the time needed to perform a surgical procedure by eliminating the need to switch between different tissue cutting instruments during the surgical procedure.

Moreover, it is an object of the present invention to provide a straightening tool of simplified construction and operation for straightening a pre-bent angled tissue cutting instrument.

The present invention also has as an object to straighten a pre-bent tissue cutting instrument in a short amount of time using a minimal number of procedural steps.

Some of the advantages of the present invention are that the pre-bent outer member of the angled tissue cutting instrument is straightened without kinking; the pre-bent outer member of the angled tissue cutting instrument is straightened while retaining its structural integrity; the proximal end of the outer member is not bent out of alignment with the powered surgical handpiece; the inner member can remain disposed within the outer member as the outer member is straightened or can be removed from the outer member prior to the outer member being straightened; the outer and inner members can remain coupled to the powered surgical handpiece as the outer member is straightened with the inner member disposed therein; the outer member is straightened without damage to the cutting edge and/or opening at its distal end; where the outer member is straightened with the inner member disposed therein, the cutting edge of the inner member is not damaged; straightening of the outer member may be accomplished by one person using a simple, two-step process; the same straightening tool can be used to straighten various angled tissue cutting instruments having pre-formed bends of various angles and radii of curvature at various locations; the straightening tool can be designed to straighten angled tissue cutting instruments of different types and/or manufacturers; the straightening tool is capable of being sterilized to medical standards to maintain the sterility of the angled tissue cutting instrument being straightened; the simplified construction of the straightening tool promotes sterilization; and the straightening tool may be reusable for repeated use or may be disposable for single patient use.

These and other objects, advantages and benefits are realized with the present invention as generally characterized in a straightening tool for straightening angled tissue cutting instruments including an elongate outer tubular member having a proximal length portion and a pre-formed bend connecting the proximal length portion to a distal length portion extending from the bend to a distal end and an elongate flexible inner member movably disposed within the outer member to cut anatomical tissue. The straightening tool comprises a handle and a positioning block extending from the handle. The handle and positioning block are coaxial with a central longitudinal axis of the straightening tool, and the positioning block has a longitudinal bore also coaxial with the central longitudinal axis for receiving the distal length portion of the outer member therethrough. The positioning block has a cavity for receiving the distal end of the outer member when the distal length portion extends through the bore. The cavity has a bottom wall adjacent the bore and has an abutment wall which serves as a stop or abutment for the outer member inserted through the bore. The positioning block has a slot extending longitudinally from the bore to a forward end wall of the positioning block, and the slot has a floor extending downwardly from the bore at an angle, such as about 5 to 7 degrees. The slot has a top opening along a top of the positioning block and a forward opening along the forward end wall, and the top opening and forward opening of the slot are in communication with one another at the forward end wall. When the distal length portion is fully inserted in the bore, the bend is confined between side walls of the slot and the proximal length portion of the outer member extends upwardly and externally from the positioning block through the top opening of the slot. The bore serves as a fulcrum allowing the proximal length portion to be manually pivoted within the slot and into abutment with the floor of the slot. Upon release of the manual pivoting force on the proximal length portion, the proximal length portion is allowed to spring back a small amount in the direction of the original pre-formed bend to obtain a longitudinally straightened outer member. The angle of the floor of the slot ensures that the longitudinally straightened outer member is completely longitudinally straight or is substantially completely longitudinally straight with only a slight positive bend in the direction of the original pre-formed bend. The straightened outer member and the inner member form a straightened tissue cutting instrument for cutting anatomical tissue.

The present invention is also generally characterized in a tissue cutting instrument system for use in surgery comprising an angled tissue cutting instrument and a straightening tool for straightening the angled tissue cutting instrument. The angled tissue cutting instrument comprises an elongate outer tubular member and an elongate inner member movably received within the outer member. The outer member has a proximal length portion and a pre-formed bend connecting the proximal length portion to a distal length portion extending from the bend to a distal end having an opening. The inner member is flexible to conform to the configuration of the outer member and has a cutting edge exposed by the opening to cut anatomical tissue when the inner member is moved within the outer member. The straightening tool comprises a handle and a positioning block coaxial with a central longitudinal axis of the straightening tool. The positioning block has an internal bore coaxial with the central longitudinal axis, the bore being disposed between and communicating with a cavity of the positioning block and a slot of the positioning block. The cavity extends longitudinally, rearwardly from the bore to a rearward internal wall of the positioning block. The slot extends longitudinally, forwardly from the bore to a forward slot opening along a forward end wall of the positioning block. The slot has a floor extending from the bore to the forward opening at a downward angle, such as 5 to 7 degrees. The slot has opposing side walls extending upwardly from the floor to a top slot opening along a top of the positioning block. The top slot opening and the forward slot opening communicate with one another at the forward end wall. The outer member is insertable in the straightening tool with the distal length portion extending through the bore to position the distal end in abutment with the rearward internal wall of the positioning block and to position the bend with the slot with the proximal length portion extending externally from the top slot opening. The bore confines the distal length portion against movement in a direction radial to the central longitudinal axis to permit the proximal length portion to be pivoted within the slot and into abutment with the floor of the slot to effect straightening of the outer tubular member whereby the straightened outer member and the inner member form a longitudinally straightened angled tissue cutting instrument.

The present invention is further characterized in a method of performing surgery comprising the steps of introducing a distal end of an angled tissue cutting instrument at an operative site in a patient's body, the angled tissue cutting instrument having an elongate outer tubular member with a proximal length portion and a pre-formed bend connecting the proximal length portion to a distal length portion extending from the bend to a distal end having an opening, and an elongate inner member disposed within the outer member and having a cutting edge exposed by the opening; positioning the cutting edge adjacent anatomical tissue to be removed; moving the inner member within the outer member to cut the anatomical tissue with the cutting edge; withdrawing the angled tissue cutting instrument from the patient's body; inserting the outer member through a longitudinal bore of a straightening tool until the distal end abuts an abutment wall of the straightening tool with the distal length portion disposed within the bore in coaxial alignment with the straightening tool, the bend disposed in a slot of the straightening tool and the proximal length portion extending externally from an opening of the slot; applying manual pressure to the proximal length portion to pivot the proximal length portion within the slot in a direction opposite the opening until the proximal length portion is in abutment with a floor of the slot extending from the bore at an angle in the direction opposite the opening; releasing the manual pressure on the proximal length portion so that the proximal length portion may spring back in the direction of the original bend to obtain a longitudinally straightened outer member; removing the straightened outer member from the straightening tool; introducing the distal end of the straightened outer member at an operative site in the patient's body with the inner member received therein to form a longitudinally straightened tissue cutting instrument; positioning the cutting edge adjacent anatomical tissue to be removed; moving the inner member within the straightened outer member to cut the anatomical tissue with the cutting edge; and withdrawing the straightened tissue cutting instrument from the patient's body.

The present invention is additionally characterized by a method of performing a combined tonsillectomy and adenoidectomy procedure comprising the steps of introducing a distal end of an angled tissue cutting instrument in the nasopharynx, the tissue cutting instrument having an elongate outer tubular member with a proximal length portion and a pre-formed bend connecting the proximal length portion to a distal length portion extending from the bend to a distal end having an opening, and an elongate inner member disposed within the outer member and having a cutting edge exposed by the opening; positioning the cutting edge adjacent an adenoid; moving the inner member within the outer member to cut tissue of the adenoid with the cutting edge; withdrawing the angled tissue cutting instrument from the patient's body; inserting the outer member in a longitudinal bore of a straightening tool such that the distal length portion is confined against radial movement with the bend disposed in a slot of the straightening tool and the proximal length portion extending externally from an opening of the slot; applying manual pressure to the proximal length portion to pivot the proximal length portion within the slot in a direction opposite the opening until the proximal length portion is in abutment with a floor of the slot extending from the bore at an angle in the direction opposite the opening; releasing the manual pressure on the proximal length portion so that the proximal length portion may spring back in the direction of the original pre-formed bend to obtain a longitudinally straightened outer member; removing the straightened outer member from the straightening tool; introducing the distal end of the straightened outer member in the patient's body with the inner member received therein to form a longitudinally straightened tissue cutting instrument; positioning the cutting edge adjacent a tonsil; moving the inner member within the straightened outer member to cut tissue of the tonsil with the cutting edge; and withdrawing the longitudinally straightened tissue cutting instrument from the patient's body.

Moreover, the present invention is generally characterized in a method of performing sinus surgery comprising the steps of introducing a distal end of an angled tissue cutting instrument in a sinus cavity in a patient's body, the tissue cutting instrument having an elongate outer tubular member with a proximal length portion and a pre-formed bend connecting the proximal length portion to a distal length portion extending from the bend to a distal end having an opening, and an elongate inner member disposed within the outer member and having a cutting edge exposed by the opening; positioning the cutting edge adjacent sinus tissue to be removed; moving the inner member within the outer member to cut the sinus tissue with the cutting edge; withdrawing the angled tissue cutting instrument from the patient's body; inserting the outer member in a longitudinal bore of a straightening tool such that the distal length portion is confined against radial movement with the bend disposed in a slot of the straightening tool and the proximal length portion extending externally from an opening of the slot; applying manual pressure to the proximal length portion to pivot the proximal length portion within the slot in a direction opposite the opening until the proximal length portion is in abutment with a floor of the slot extending downwardly from the bore at an angle in the direction opposite the opening; releasing the manual pressure on the proximal length portion so that the proximal length portion may spring back in the direction of the original pre-formed bend to obtain a longitudinally straightened outer member; removing the straightened outer member from the straightening tool; introducing the distal end of the straightened outer member in the sinus cavity with the inner member received therein to form a longitudinally straightened tissue cutting instrument; positioning the cutting edge adjacent sinus tissue to be removed; moving the inner member within the straightened outer member to cut the sinus tissue with the cutting edge; and withdrawing the longitudinally straightened tissue cutting instrument from the patient's body.

The present invention is also characterized in a method of performing surgery comprising the steps of selecting an angled tissue cutting instrument having an elongate outer tubular member manufactured or fabricated with a pre-formed bend connecting a proximal length portion of the outer member to a distal length portion of the outer member extending from the bend to a distal end having an opening, and an elongate inner member disposed within the outer member and having a cutting edge exposed by the opening; inserting the outer member through a longitudinal bore of a straightening tool until the distal end abuts an abutment wall of the straightening tool with the distal length portion disposed within the bore in coaxial alignment with the straightening tool, the bend disposed in a slot of the straightening tool and the proximal length portion extending externally from an opening of the slot; applying manual pressure to the proximal length portion to pivot the proximal length portion within the slot in a direction opposite the opening until the proximal length portion is in abutment with a floor of the slot extending from the bore at an angle in the direction opposite the opening; releasing the manual pressure on the proximal length portion so that the proximal length portion may spring back in the direction of the original bend to obtain a longitudinally straightened outer member; removing the straightened outer member from the straightening tool; introducing the distal end of the straightened outer member at an operative site in the patient's body with the inner member received therein to form a longitudinally straightened tissue cutting instrument; positioning the cutting edge adjacent anatomical tissue to be removed; moving the inner member within the straightened outer member to cut the anatomical tissue with the cutting edge; and withdrawing the straightened tissue cutting instrument from the patient's body.

BRIEF DESCRIPTION OF THE DRAWINGS

FIG. 1 is a side view of an angled tissue cutting instrument or blade.

FIG. 2 is an exploded side view, partly in section, of the angled tissue cutting instrument.

DESCRIPTION OF THE PREFERRED EMBODIMENTS

Figure 3:
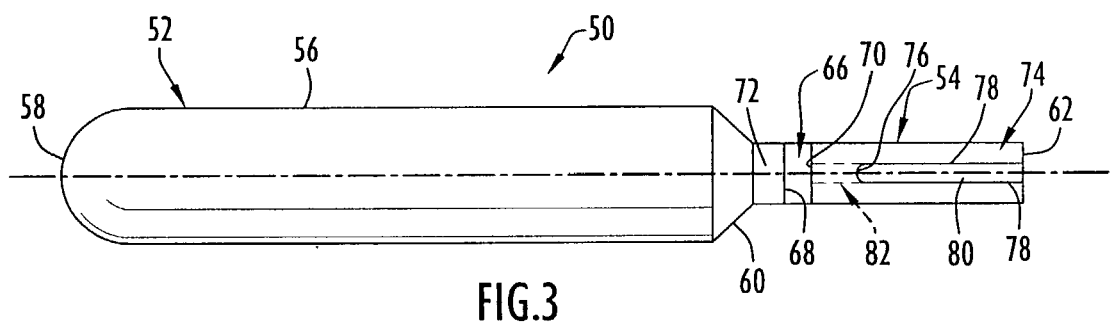
FIG. 3 is a top view of a straightening tool for straightening an angled tissue cutting instrument.

The present invention relates to a straightening or unbending tool or apparatus for straightening or unbending an angled tissue cutting instrument such as the angled tissue cutting instrument 10 illustrated in FIGS. 1 and 2. The angled tissue cutting instrument or blade 10 illustrated in FIGS. 1 and 2 includes an elongate outer tubular member 12 and an elongate inner member 14 rotatably or movably disposed with the outer member. Outer member 12, which may be considered an outer blade member, is an outer tubular member or sleeve having a proximal end coupled to an outer member hub 16. The outer tubular member 12 has a proximal length portion 18 of longitudinally or axially straight configuration extending distally from the outer member hub to a bend, curve or angle 20 connecting the proximal length portion with a distal length portion 22 oriented at an angle A relative to the central longitudinal axis 24 of the proximal length portion. The distal length portion 22 is of longitudinally or axially straight configuration extending distally from bend 20 to a distal end 26 having an opening 28, and the angle A is defined between a central longitudinal axis 30 of the distal length portion and the central longitudinal axis 24.

The outer member 12 is essentially a rigid member formed by bending a solid, continuous and unbroken tubular member of uniform wall thickness, such that the bend, curve or angle 20 is pre-formed therein as part of the fabrication or manufacturing process. The orientation of opening 28 as well as the angle, the radius of curvature and the location of the bend 20 are dependent on the surgical procedure to be performed. The angled tissue cutting instrument 10 is particularly designed for use as an adenoid blade with the distal length portion 22 extending from bend 20 at an angle A of about 40 degrees relative to the central longitudinal axis 24, the bend 20 having a radius of curvature R of about 0.875 inch and a location about 0.7 inch from the distal end 26, and the opening 28 facing outwardly relative to the direction of the bend, i.e. relative to the center of curvature for the bend. The outer member 12 is typically made of a medically acceptable metal such as stainless steel.

Inner member 14, which may be considered an inner blade member, may be tubular or non-tubular but is shown as being tubular in the case of instrument 10. Inner member 14 has a proximal length region 32 extending distally from an inner member hub 34, a distal end formed as or provided with a cutting tip 36 and a flexible or bendable region 38 between proximal length region 32 and cutting tip 36. The cutting tip 36 is adapted to cut anatomical tissue, and the cutting tip for inner member 14 includes an opening 40 communicating with a lumen 42 through the inner member and a cutting edge 44 along a peripheral edge of opening 40. The cutting edge 44 may be designed in various ways, for example as a sharp peripheral edge of opening 40 or a plurality of cutting teeth along a peripheral edge of the opening 40 as shown for inner member 14. When the inner member 14 is disposed within the outer member 12 as shown in FIG. 1, the inner member extends through the outer member hub 16 with the inner member hub 34 disposed proximally of the outer member hub, the cutting edge 44 is exposed by the opening 28 of outer member 12, and the flexible region 38 is disposed within or adjacent the bend 20 so that the inner member follows or conforms to the longitudinally or axially bent, curved or angled configuration of the outer member. The proximal length region 32 is rigid and transmits torque from a powered surgical handpiece, shown at 84 in FIG. 6, via the flexible region 38 to rotate the cutting tip 36 when the inner member 14 is rotated relative to and within the outer member 12 by the powered surgical handpiece. The flexible region 38 allows the inner member 14 to conform to the angled configuration of the outer member 12 as it is rotated relative to and within the outer member. The hubs 16 and 34 are adapted to be removably coupled with the powered surgical handpiece, and the powered surgical handpiece may be of the type disclosed in U.S. Pat. No. 5,916,231 to Bays, the entire disclosure of which is incorporated herein by reference. Depending on the design of the angled tissue cutting instrument, the inner member may or may not be removable from the outer member.

The cutting tip 36 can have various configurations depending on the surgical procedure to be performed. The cutting tip 36 accesses anatomical tissue at an operative site via the opening 28 of outer member 12 and is aligned with or disposed adjacent the opening 28 when the inner member 14 is rotatably received in the outer member 12. The distal end 26 of the outer member 12 can be provided with or without a cutting edge. In the case of instrument 10, the distal end 26 of outer member 12 is shown as having a cutting edge 46 cooperable with the cutting edge 44 of inner member 14 to cut anatomical tissue as the inner member is rotated within the outer member. The cutting edge 46 may likewise be designed in various ways, for example as a sharp peripheral edge of opening 28 or as a plurality of cutting teeth along a peripheral edge of the opening 28 as shown in FIGS. 1 and 2. The cutting edge 44 moves past the cutting edge 46 as the inner member is rotated within the outer member to cut anatomical tissue. Anatomical debris may be aspirated from the operative site through the lumen 42 of inner member 14, the opening 40 of the inner member forming a suction inlet through which debris is aspirated. Where the powered surgical handpiece of the aforementioned Bays patent is used, the debris is aspirated through the inner member and the handpiece. The flexible region of the inner member can be formed in various ways, the flexible region 38 being formed by way of example of a reinforced polymeric material. For use as an adenoid blade, the angled tissue cutting instrument 10 may be a RADenoid® Blade of Medtronic Xomed Surgical Products, as represented by U.S. Pat. No. 5,922,003 to Anctil et al, the entire disclosure of which is incorporated herein by reference.

The angled tissue cutting instrument may comprise an instrument of the type disclosed in U.S. patent application Ser. No. 09/404,461 filed Sep. 24, 1999, the entire disclosure of which is incorporated herein by reference, with a flexible region formed by a helical cut in the tubular inner member and at least one strip of material spirally wound over the helical cut. The angled tissue cutting instrument may comprise an instrument of the type disclosed in U.S. patent application Ser. No. 09/950,607 filed Sep. 13, 2001, the entire disclosure of which is incorporated herein by reference, with a flexible region formed by a helical cut formed in the tubular inner member in a dovetail pattern and at least one spiral wrap disposed over the helical cut. As described further below, the angled tissue cutting instrument may be a sinus blade such as the RAD® 40 Curved Blade or the RAD 60 X-TREME™ Curved Blade of Medtronic Xomed Surgical Products.

Aspiration may be accomplished in the angled tissue cutting instrument through the inner member, through the outer member, such as between the outer member and the inner member, or in any other suitable manner. However, it should be appreciated that the angled tissue cutting instrument can be provided and/or used without aspiration. The angled tissue cutting instrument may be provided with or without an irrigation passage or channel for supplying irrigating or flushing fluid to the operative site and both aspiration and irrigation may be provided in the angled tissue cutting instrument. Irrigation may be provided along the instrument in various ways including through the inner member, through the outer member, such as between the outer member and the inner member, externally along the outer member, or in any other suitable manner. In the instrument 10, for example, the outer member hub 16 has an optional nipple 48 extending proximally from a side of the outer member hub at an acute angle relative to the central longitudinal axis 24 and communicating with an annular space between the outer member 12 and the inner member 14. When a source of irrigating or flushing fluid is connected with the nipple 48, the fluid will be supplied to the operative site via the opening 28, for example to irrigate the site or clear blockages. The angled tissue cutting instrument may include an external irrigation channel as disclosed in U.S. Pat. No. 5,782,795 to Bays and U.S. Pat. No. 6,312,438 B1 to Adams, the entire disclosures of which are incorporated herein by reference. The Adams patent is also representative of a burr tip which may be used as the cutting tip in the angled tissue cutting instrument and of an aspiration passage and aspiration ports which may be incorporated in the inner member.

Although the straightening tool of the present invention is particularly desirable for use with a curved, bent or angled adenoid blade, as represented by the angled tissue cutting instrument 10 and by the RADenoid® Blade of Medtronic Xomed Surgical Products, and with a curved, bent or angled sinus blade as represented by the RAD 40® Curved Blade and RAD 60 X-TREME® Curved Blade of Medtronic Xomed Surgical Products, it should be appreciated that the straightening tool can be used or adapted for use with various other types of curved, bent or angled tissue cutting instruments of various manufacturers. In particular, the straightening tool can be adapted for use with laryngeal blades, as represented by the Skimmer Angle-Tip blades and the Tricut™ Angle-Tip blades of Medtronic Xomed Surgical Products, used by way of example for supraglottic and subglottic papilloma removal or debulking, tumor debulking, tracheal stenosis and transsphenoidal hypophysectomy.

Figure 4:
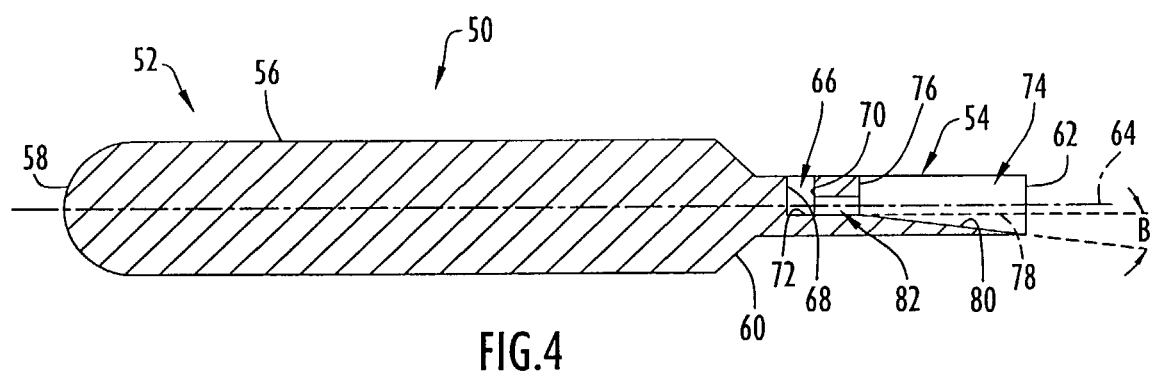
FIG. 4 is a longitudinal sectional view of the straightening tool.
Figure 5:
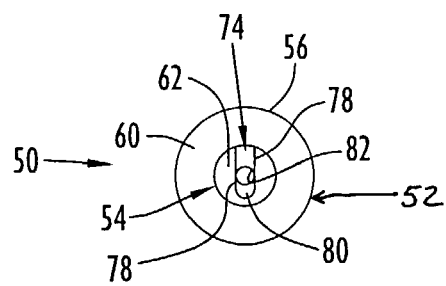
FIG. 5 is an end view of the straightening tool.

The straightening tool or apparatus 50 according to the present invention is illustrated in FIGS. 3, 4 and 5 and is integrally, unitarily or monolithically formed as one piece with no moving parts. The tool 50 includes a handle 52 and a positioning block 54 extending forwardly from the handle. The handle 52 comprises an elongate cylindrical section 56 rearwardly joined to a partial spherical rearward end 58 and forwardly joined to a tapered forward end or neck 60. The forward end 60 has a truncated conical configuration tapering in the forward direction from the external diameter of cylindrical section 56 to positioning block 54. The cylindrical section 56 may be provided with external ridges or grooves to facilitate grasping and/or the handle 52 may have various ergodynamic external configurations. The positioning block 54 has a generally cylindrical external configuration extending from the handle forward end 60 to a forward end wall 62 of the positioning block, and the cylindrical external configuration of the positioning block has an external diameter smaller than the external diameter of the cylindrical section 56. The straightening tool 50 has a central longitudinal axis 64, coaxial with the positioning block 54 and the handle 52.

A cavity 66 is formed in the positioning block 54 and is bounded rearwardly by an internal rearward or abutment wall 68 of the positioning block, forwardly by an internal rearward intermediate wall 70 of the positioning block and inferiorly by an internal bottom wall 72 of the positioning block. The rearward and rearward intermediate walls 68 and 70 are planar and parallel and are perpendicular to the central longitudinal axis 64. The bottom wall 72 is flat or planar but may be curved to cradle the distal end of the outer member of the angled tissue cutting instrument. The bottom wall 72 connects the rearward and rearward intermediate walls 68 and 70 and is perpendicular thereto. The cavity 66 has a partial circular configuration in cross-section and is open along the top and opposing sides of positioning block 54. The bottom wall 72 is spaced radially from the central longitudinal axis 64 in a downward direction, and the cavity 66 is open along an opening that follows the external cylindrical configuration of the positioning block and extends arcuately between lateral edges of the bottom wall 72. The rearward intermediate wall 70 is spaced forwardly from the abutment wall 68 by a distance in the longitudinal or axial direction sufficient to accommodate the cutting edge or edges of the angled tissue cutting instrument therebetween as explained further below.

A longitudinal unbending slot 74 is formed in positioning block 54 and extends rearwardly from forward end wall 62 to an internal forward intermediate wall 76 of positioning block 54. The slot 74 is open at its top via a top slot opening along the top of the positioning block and at its forward end via a forward slot opening along forward end wall 62. The top and forward slot openings are in communication with each other where they meet along the forward end wall 62. Slot 74 is bounded rearwardly by forward intermediate wall 76, laterally by opposing internal side walls 78 and inferiorly by an internal contact surface or floor 80. The forward intermediate wall 76 is spaced forwardly from the rearward intermediate wall 70 and may be curved as shown in FIG. 3. The side walls 78 are planar and parallel and extend forwardly from forward intermediate wall 76 to the forward slot opening along the forward end wall 62. The floor 80 is curved with a partial circular or partial cylindrical configuration between side walls 78, the side walls 78 extending upwardly from floor 80 to the top slot opening along the top of the positioning block. The central longitudinal axis 64 is centered between the side walls 78 and thusly bisects the slot 74 longitudinally.

A longitudinal bore 82 is formed in positioning block 54 between cavity 66 and slot 74. The bore 82 has an opening along rearward intermediate wall 70 adjacent the bottom wall 72 and an opening along forward intermediate wall 76 adjacent floor 80 to establish communication between cavity 66 and slot 74. The bore 82 defines a confinement passage in tool 50 for receiving and confining the distal length portion of outer member 12, and the confinement passage, cavity 66 and unbending slot 74, comprise an unbending channel for tool 50. The bore 82 has a cylindrical configuration coaxial with the central longitudinal axis 64 and tangential to a plane containing bottom wall 72 of cavity 66. The bore 82 has a diametric or cross-sectional dimension to receive the external diametric or cross-sectional configuration of outer member 12, preferably with a close fit. The bore 82 extends diametrically between the side walls 78 and preferably the bore is tangential to the planes of side walls 78, respectively, such that the width of slot 74 is the same as or substantially the same as the bore diameter. The floor 80 of slot 74 is angled downwardly from the bore 82 in a direction opposite the top slot opening and forms angle B with the plane of bottom wall 72 as shown in FIG. 4. Particularly, a plane tangential to the curved floor 80 forms angle B with the plane of bottom wall 72. Angle B is preferably in the range of five to seven degrees and is 5° for one preferred embodiment. The radial curvature for floor 80 is preferably the same or substantially the same as the radial curvature of the bore 82.

The straightening tool 50 is preferably made of a medically acceptable material, including metals, such as stainless steel, ULTEM, ABS, PEEK and LEXAN, for example, having sufficient strength to effect straightening of the angled tissue cutting instrument as explained further below. The straightening tool 50 may be fabricated by molding. The straightening tool 50 may be designed for sterilization to medical standards for repeated use or may be disposable after each use. The straightening tool 50 has no moving parts or inaccessible recesses such that proper sterilization is greatly facilitated.

In one representative straightening tool for use with the RADenoid® Blade of Medtronic Xomed Surgical Products, the straightening tool has an overall length of about 6.21 inches; the handle has an overall length of about 4.27 inches; the neck extends about 0.24 inch forwardly from the cylindrical section of the handle at about a 45 degree angle or taper relative to the external diameter of the cylindrical section; the positioning block has a length of about 1.94 inches; the rearward wall is about 4.5 inches forwardly of the rearward end of the handle; the longitudinal distance between the rearward wall and the rearward intermediate wall is about 0.23 inch; the length of the slot is about 1.06 inches; the width of the slot is about 0.161 inch; the distance between the rearward wall and the forward end wall is about 1.71 inches; the bore has a diameter of about 0.161 inch; angle B is 5 degrees; the cylindrical section has an external diameter of about 1.0 inch; the positioning block has an external diameter of about 0.53 inch; and the plane of the bottom wall of the cavity is spaced radially about 0.080 inch from the central longitudinal axis. The representative straightening tool can also be used to straighten the RAD 40® Curved Blade and the RAD 60 X-TREME™ Curved Blade of Medtronic Xomed Surgical Products as explained further below.

Figure 6:
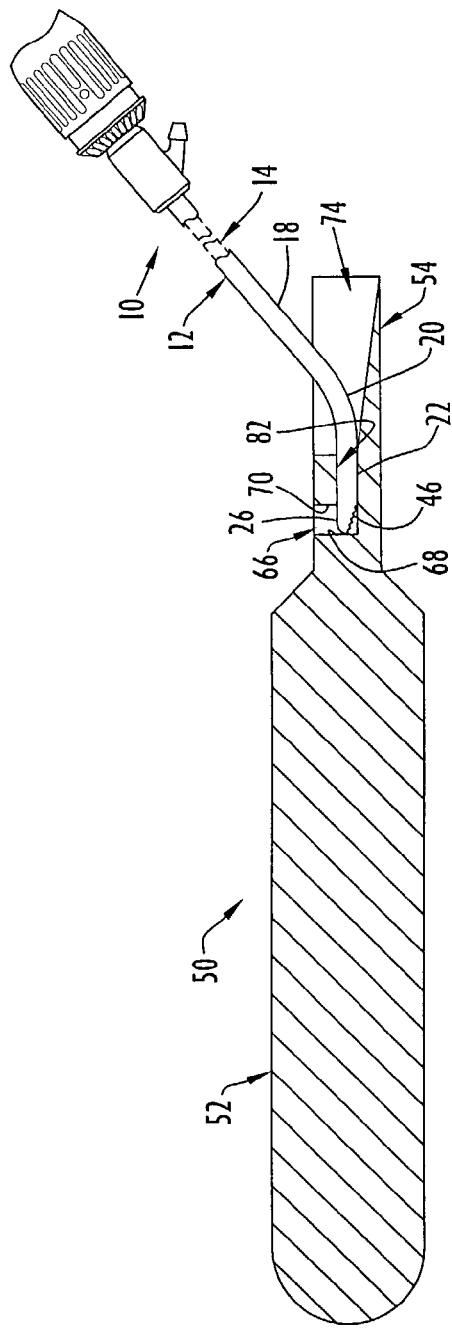
FIG. 6 is a side view, partly in section, illustrating an outer member of the angled tissue cutting instrument of FIG. 1 inserted in a positioning block of the straightening tool.
Figure 7:
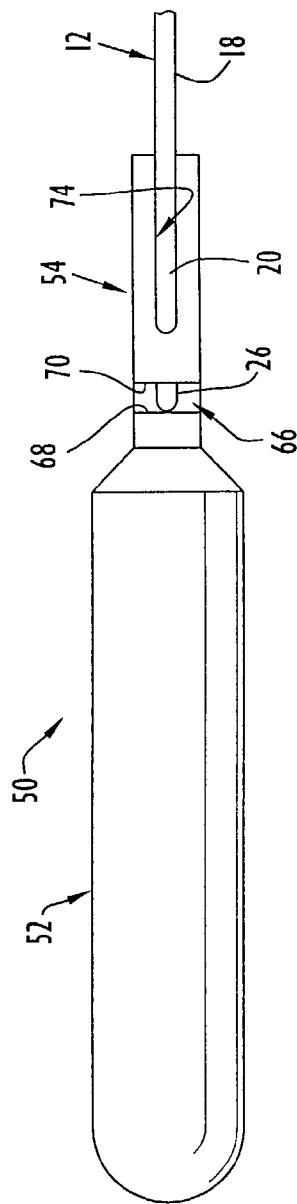
FIG. 7 is a top view depicting the outer member of the angled tissue cutting instrument of FIG. 1 inserted in the positioning block.

A method of straightening or unbending the angled tissue cutting instrument 10 using the straightening tool 50 is illustrated in FIGS. 6–10. As shown in FIGS. 6 and 7, the distal end 26 of outer member 12 is inserted in the slot 74 and is advanced through bore 82 until the outer member distal end contacts the rearward wall 68 and is fully received in the cavity 66. Contact of the distal end 26 with the rearward wall 68 can be felt tactilely, and the opening into cavity 66 allows abutment of the outer member distal end with the rearward wall 68 to be visualized to ensure that the outer member 12 is properly inserted in the straightening tool 50. The distal end 26 of the outer member 12 can be positioned in the cavity 66 through bore 82 by a single person using one hand to grasp the handle 52 and the other hand to manipulate the outer member 12. The distal end of the outer member 12 can be positioned in the positioning block 54 with the inner member 14 withdrawn from the outer member, where the design of the instrument permits withdrawal or removal of the inner member from the outer member as shown by solid lines in FIG. 6, or with the inner member disposed within the outer member as shown in dotted lines in FIG. 6. The inner and outer members may be uncoupled from the powered surgical handpiece prior to positioning the outer member in the cavity 66, or the inner and outer members may remain coupled to the powered surgical handpiece 84 when the outer member distal end is positioned in the positioning block as also shown in FIG. 6.

The opening 28 and the length of the cutting edge 46, where provided, is/are accommodated between the rear wall 68 and the rearward intermediate wall 70 so that the opening and/or the cutting edge of the outer member is/are protected and not damaged during bending. Where the inner member 14 remains disposed within the outer member 12, the opening 40 and the length of cutting edge 44 of the inner member are accommodated between the rearward wall 68 and the rearward intermediate wall 70 so that the opening and the cutting edge of the inner member are protected and not damaged during unbending or straightening of the outer member. The external diameter of the outer member is received in the bore 82 with a close fit, and the cylindrical wall of the positioning block 54 forming bore 82 confines the outer member against radial movement, i.e. movement radial to central longitudinal axis 64. The distal length portion 22 of the outer member is thusly coaxially aligned with the straightening tool 50, and the bend 20 is disposed in slot 74 with the distal length portion confined in the confinement passage. The proximal length portion 18 extends upwardly from the bend 20 and extends externally from the positioning block 54 through the top slot opening of slot 74. The bend 20 and part of the proximal length portion 18 are confined against lateral movement between the side walls of slot 74.

Figure 8:
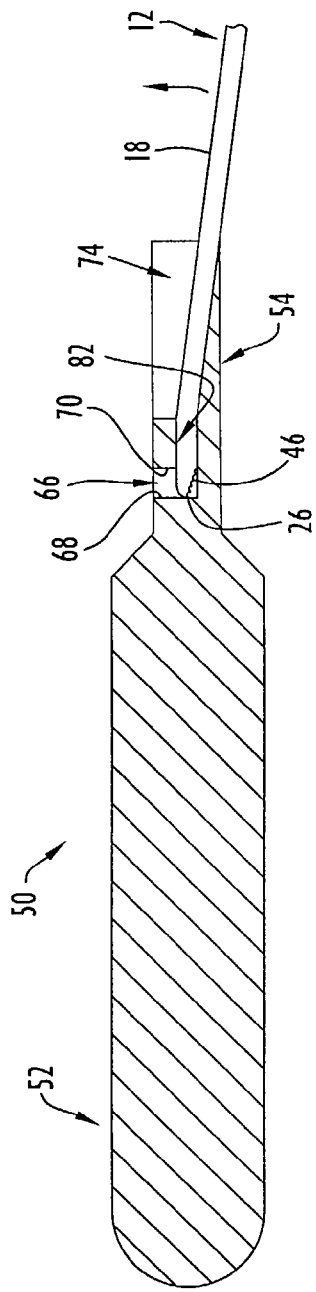
FIG. 8 is a side view, partly in section, depicting use of the straightening tool to straighten the outer member of the angled tissue cutting instrument.

Once the distal length portion of outer member 12 is positioned in the confinement passage with the distal end 26 in abutment with the rearward wall 68, the proximal length portion 18 of outer member 12 that extends externally from the slot 74 is moved, pivoted or rotated manually with the hand in a direction opposite the bend 20, i.e. downwardly looking at FIGS. 6 and 8, until the proximal length portion 18 contacts or abuts the floor 80 of slot 74 as shown in FIG. 8. The proximal length portion 18 is moved along the top slot opening and along the forward slot opening, with the side walls of slot 74 guiding the proximal length portion 18 as it is moved downwardly to the floor 80 to prevent misalignments. The curved configuration of the floor 80 mates with the external curvature of the outer member 12 to ensure proper abutment of the outer member with the floor. The bore 82 acts as a fulcrum about which the outer member is pivoted, and no force or pressure is exerted on the distal end 26 of the outer member so that the opening 28 and/or the cutting edge 46 thereof are protected and not damaged. Where the inner member 14 is disposed within the outer member 12 during straightening, the flexible region of the inner member allows the inner member to follow or conform to the configurations of the outer member during straightening. As shown in FIG. 8, movement of the proximal length portion 18 into contact with floor 80 results in the outer member 12 being reverse bent due to the angle of floor 80 in a direction opposite the initial bend 20.

Figure 9:
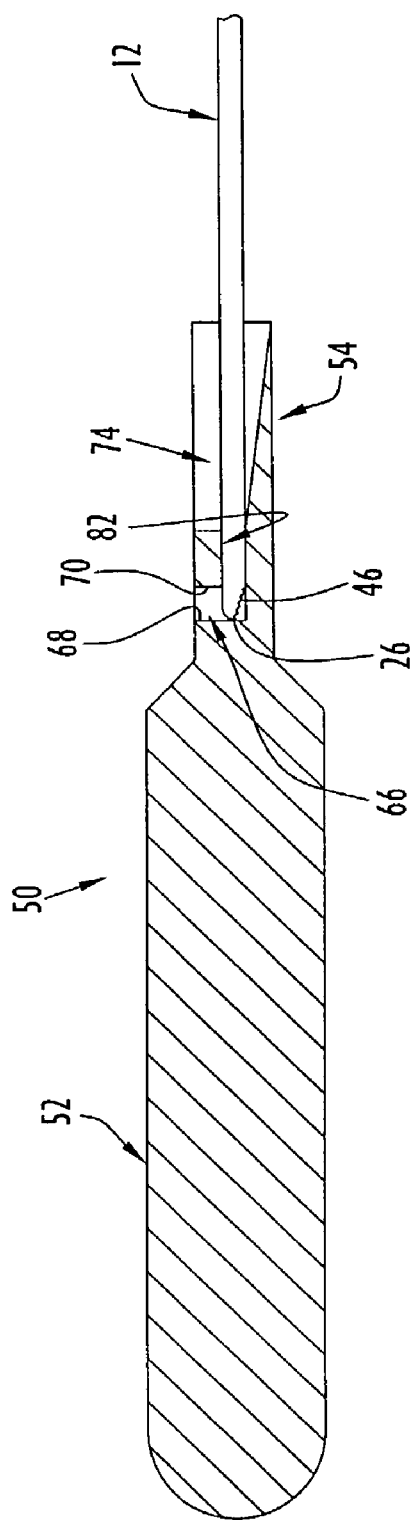
FIG. 9 is a side view, partly in section, showing the outer member of the angled tissue cutting instrument straightened by the straightening tool in a first manner.
Figure 10:
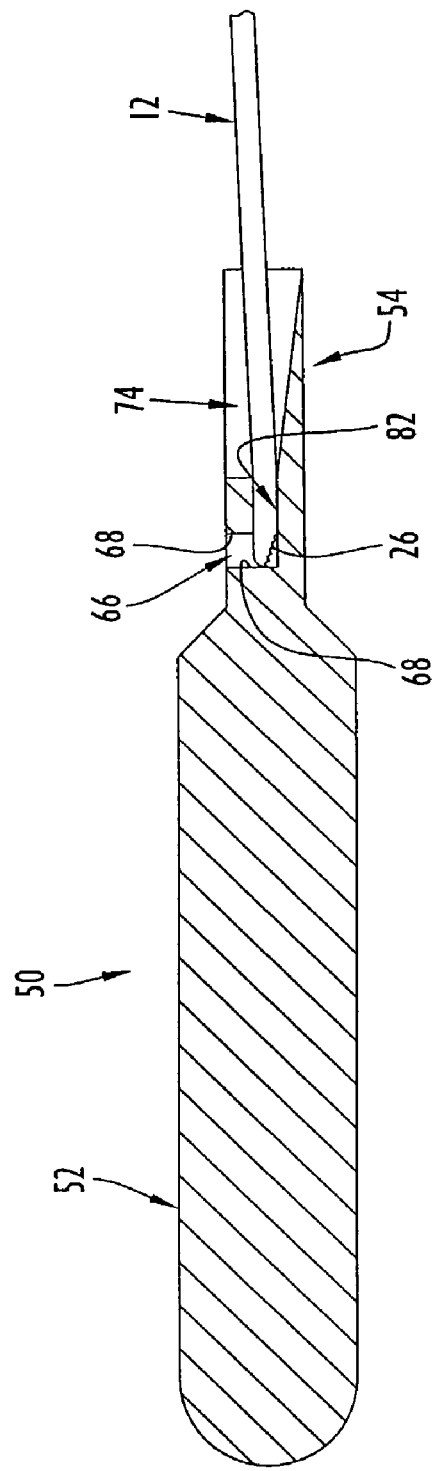
FIG. 10 is a side view, partly in section, illustrating the outer member of the angled tissue cutting instrument straightened by the straightening tool in a second manner.

Upon abutment of the proximal length portion 18 with the floor 80, manual force or pressure on the proximal length portion in the direction opposite the original bend 20 is released, and the proximal length portion will spring back a small amount from floor 80 in the direction of the original bend, as shown by the arrow in FIG. 8, due to the spring memory of the outer member. The angle B ensures that the outer member 12, after springing back from floor 80, assumes a longitudinally or axially straightened configuration in which the outer member is completely longitudinally or axially straight as shown in FIG. 9 or is substantially longitudinally or axially straight with only a slight positive bend, curve or angle in the direction of the original bend as shown by FIG. 10. Accordingly, "unbending" and "straightening" as used herein refer to a complete unbending or straightening in which the outer member is rendered completely longitudinally or axially straight or a substantially complete unbending or straightening in which the outer member is rendered substantially completely longitudinally or axially straight. The extent to which the proximal length portion 18 springs back and, therefore, the size of any residual positive bend, curve or angle, will depend on the spring memory characteristics of the particular outer member.

Straightening or unbending of the outer member 12 is accomplished using the straightening tool 50 in a minimal number of simple procedural steps, i.e. a first procedural step in which the outer member is manually positioned in the tool and a second procedural step in which the outer member is manually pivoted and reverse bent in a direction opposite the original bend, curve or angle. Once straightening has been accomplished, the outer member need only be withdrawn from the positioning tool by pulling the outer member away from the straightening tool in the longitudinal or axial direction. If necessary, the straightened outer member is reassembled with the inner member to form a longitudinally or axially straightened tissue cutting instrument, and the reassembled inner and outer members are reattached to the powered surgical handpiece. Of course, where the powered surgical handpiece 84 remains attached to the inner and outer members during straightening, the longitudinally straightened tissue cutting instrument is ready for further use upon withdrawal from the straightening tool.

Figure 11:
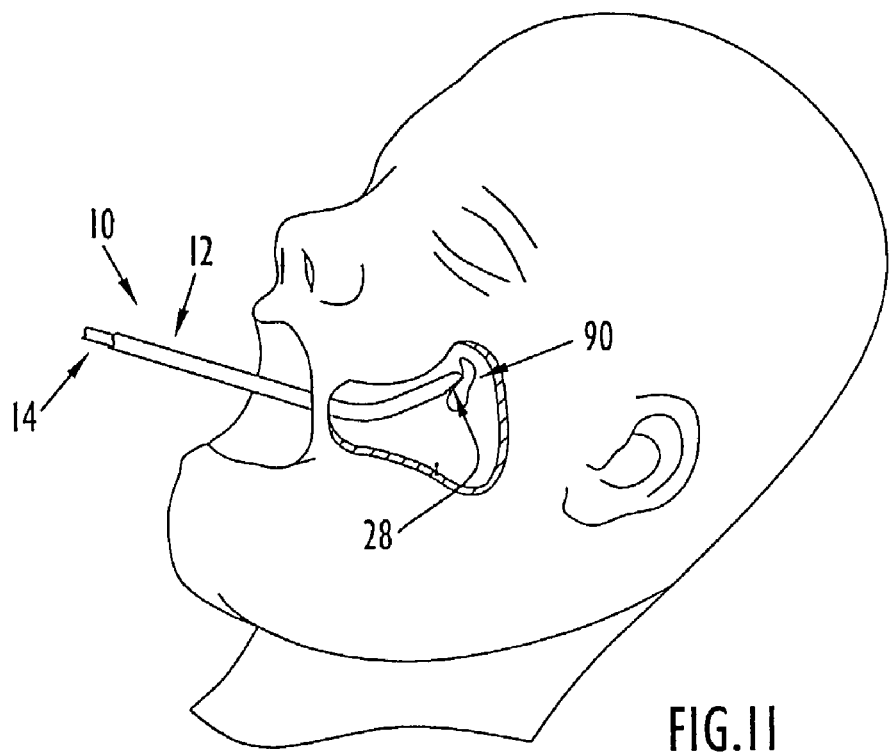
FIG. 11 depicts an adenoidectomy performed using the angled tissue cutting instrument of FIG. 1 in a T&A procedure.
Figure 12:
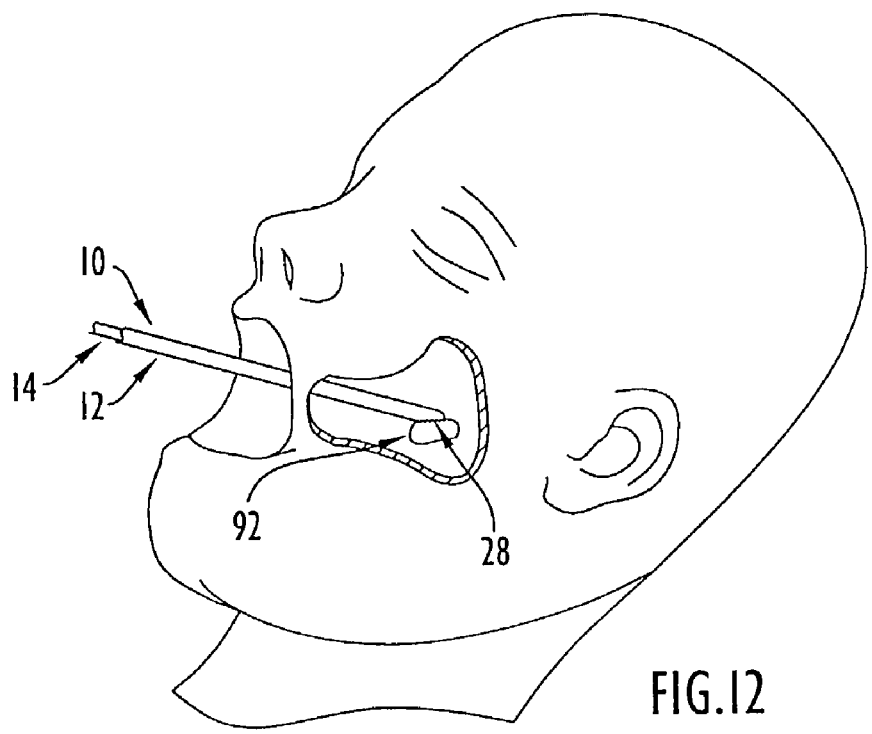
FIG. 12 shows the straightened tissue cutting instrument obtained by straightening the angled tissue cutting instrument subsequent to the adenoidectomy and used to perform a tonsillectomy in the T&A procedure.

The straightening procedure may be performed during a surgical procedure wherein an angled tissue cutting instrument and the straightening tool 50 are provided as a tissue cutting instrument system or apparatus. The angled tissue cutting instrument is used during the surgical procedure to remove anatomical tissue at an operative site, the angled tissue cutting instrument is subsequently straightened or unbent during the surgical procedure to obtain a longitudinally or axially straightened tissue cutting instrument, and the straightened tissue cutting instrument is thereafter used in the surgical procedure to further remove anatomical tissue. FIGS. 11 and 12 are illustrative of a surgical procedure, particularly a combined tonsillectomy and adenoidectomy procedure (T&A procedure), using a tissue cutting instrument system including the angled tissue cutting instrument 10 and the straightening tool 50. FIG. 11 illustrates the angled tissue cutting instrument or adenoid blade 10 inserted through a patient's mouth to perform an adenoidectomy. The distal end of the angled tissue cutting instrument 10 is introduced into the nasopharynx with the opening 28 facing an adenoid 90. The adenoidectomy is initiated in the anterior nasopharynx, near the choana. The inner member 14 is rotated within the outer member 12 by the powered surgical handpiece 84, and the cutting edges 44 and 46 remove adenoid tissue. Removal of adenoid tissue is initiated using a light touch with the adenoid blade, with tissue removal being accomplished by moving the blade side-to-side and/or sweeping the blade anterior to posterior. Sweeping the blade anteriorly to posteriorly is particularly effective along the torus tubarius. The adenoid blade is predictably sharp for every case, allowing a precise progressive removal of adenoid tissue while simultaneous suction or aspiration evacuates blood and tissue from the operative site for enhanced visualization. Tissue at the superior choana and along the torus tubarius can be shaved away to effect a more thorough adenoidectomy which minimizes the potential for tissue regrowth and symptom recurrence. Continuous suction through the inner member keeps the surgical field visible while tissue is removed from difficult areas such as the superior choana and along the posterior torus tubarius. The precise shaving action of the adenoid blade removes well-defined portions of tissue exactly where the blade is placed. The increased surgical accuracy allows easy removal of hypertrophic adenoid tissue from the posterior nasal cavity and along the torus. The curved, bent or angled configuration of the adenoid blade greatly enhances access to the operative site.

Upon completion of the adenoidectomy, the instrument 10 is withdrawn from the patient's mouth, and the outer member 12 is inserted in the straightening tool 50 as described in connection with FIGS. 6–10. The straightening tool 50 will be sterile so that the instrument 10 is not contaminated. The outer member 12 is straightened as described for FIGS. 6–10 to obtain a longitudinally or axially straightened tissue cutting instrument, and the straightened tissue cutting instrument 10 is inserted in the patient's mouth to perform a tonsillectomy as shown in FIG. 12. The opening 28 of the outer member 12 is positioned adjacent a tonsil 92, and the straightened configuration of the tissue cutting instrument 10 enhances access to the tonsil 92. The inner member 14 is rotated within the outer member 12 via the powered surgical handpiece 84, and the cutting edges 44 and 46 remove anatomical tissue of the tonsil while suction or aspiration is effected through the inner member 14. Upon completion of the tonsillectomy, the straightened tissue cutting instrument 10 is withdrawn from the patient's mouth.

Figure 13:
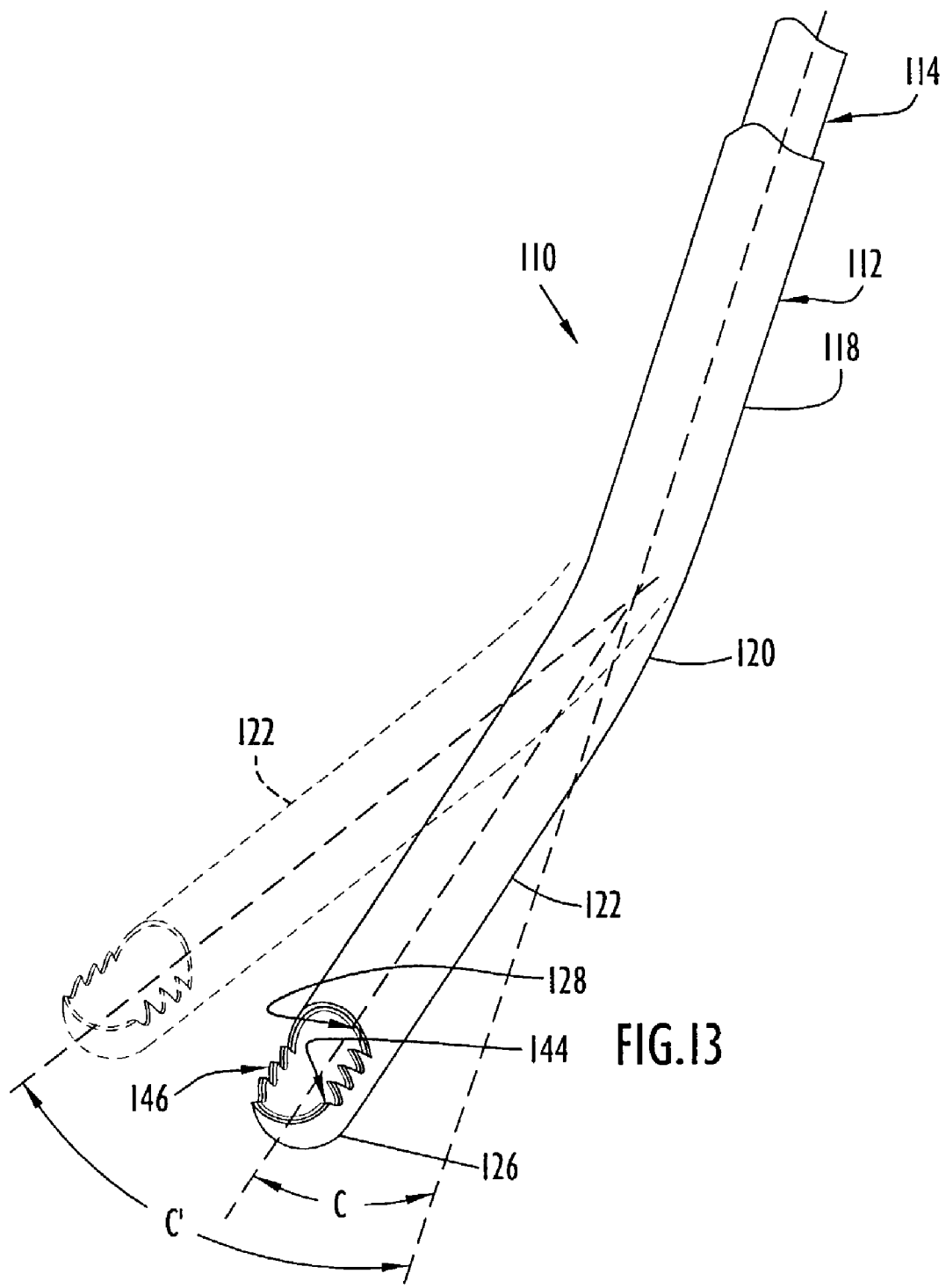
FIG. 13 is a side view of an alternative angled tissue cutting instrument or blade.

An alternative angled tissue cutting instrument 110 for use with straightening tool 50 is shown in FIG. 13. Instrument 110 is similar to instrument 10 except that the opening 128 of outer member 112 faces in the direction of the center of curvature for bend 120. The angled tissue cutting instrument 110 corresponds to the RAD® 40 Curved Blade of Medtronic Xomed Surgical Products and has an angle C of about 40° between proximal length portion 118 and distal length portion 122. The angled tissue cutting instrument 110 may be provided with an angle C' of about 60° between proximal length portion 118 and distal length portion 122 as shown in dotted lines in FIG. 13 and as corresponds to the RAD 60 X-TREME™ Curved Blade of Medtronic Xomed Surgical Products. The angled tissue cutting instrument 110 is particularly advantageous for use as a sinus blade in sinus surgery to access the frontal recess and maxillary sinus, for ethmoid and frontal recess surgery, maxillary polyp removal, uncinectomy and antrostomy, for example.

Figure 14:
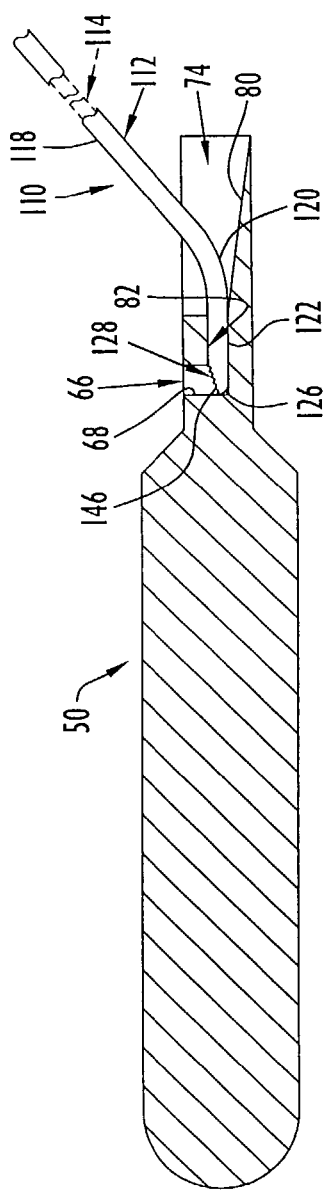
FIG. 14 is a side view, partly in section, illustrating an outer member of the angled tissue cutting instrument of FIG. 14 inserted in the positioning block of the straightening tool.
Figure 15:
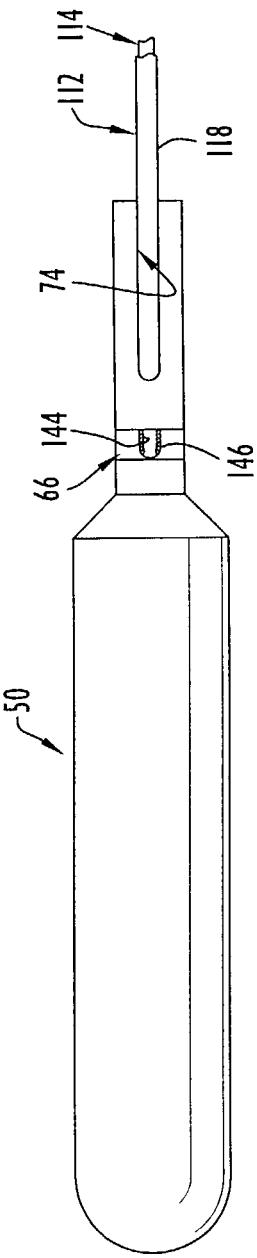
FIG. 15 is a top view depicting the outer member of the angled tissue cutting instrument of FIG. 14 inserted in the positioning block.
Figure 16:
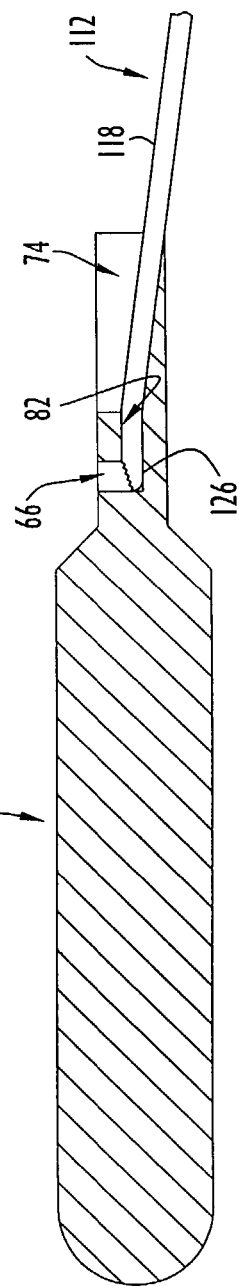
FIG. 16 is a side view, partly in section, depicting use of the straightening tool to straighten the outer member of the angled tissue cutting instrument of FIG. 14.
Figure 17:
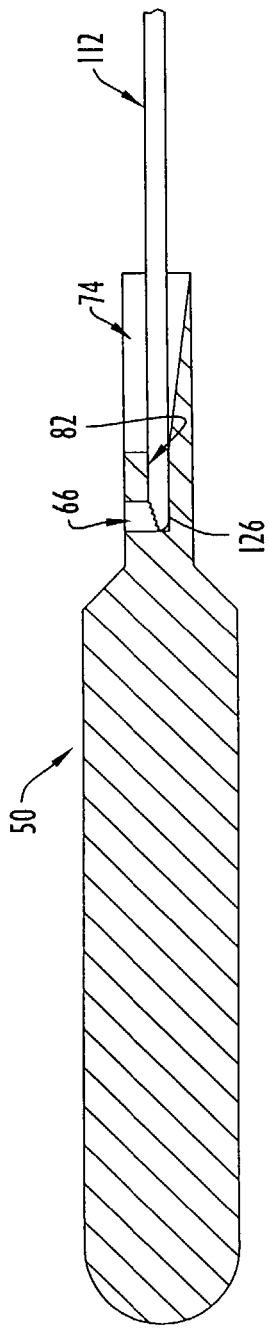
FIG. 17 is a side view, partly in section, showing the straightened outer member of the tissue cutting instrument of FIG. 14.

FIGS. 14 and 15 depict the angled tissue cutting instrument 110 inserted in the straightening tool 50 with the distal end 126 of outer member 112 in abutment with the rearward wall 68 as described above for angled tissue cutting instrument 10 except that the opening 128 and cutting edge 146 for outer member 112 face upwardly in the cavity 66. FIG. 15 shows the inner member 114 of instrument 110 disposed within the outer member 112 with the cutting edge 144 of the inner member also facing upwardly in cavity 66. The cutting edge 144 and 146 face the opening of the cavity 66 and are thusly protected from damage when the proximal length portion 118 of the outer member 112 is moved, pivoted or rotated downwardly toward floor 80. Also, the distal end of the outer member 112 is supported upon the bottom wall of the cavity 66 since the bottom wall is tangential to the bore 82. FIG. 16 shows the proximal length portion 118 manually moved, pivoted or rotated downwardly into contact with the floor 80 of slot 74 as described above for angled tissue cutting instrument 10. Once the proximal length portion 118 has been moved downwardly into abutment with floor 80 and the manual pressure or force on the proximal length portion 118 in the direction opposite the bend 120 is thereafter released, the proximal length portion 118 springs back somewhat as shown in FIG. 17. As a result, the outer member 112 is longitudinally or axially straightened as described above for outer member 12.

Figure 18:
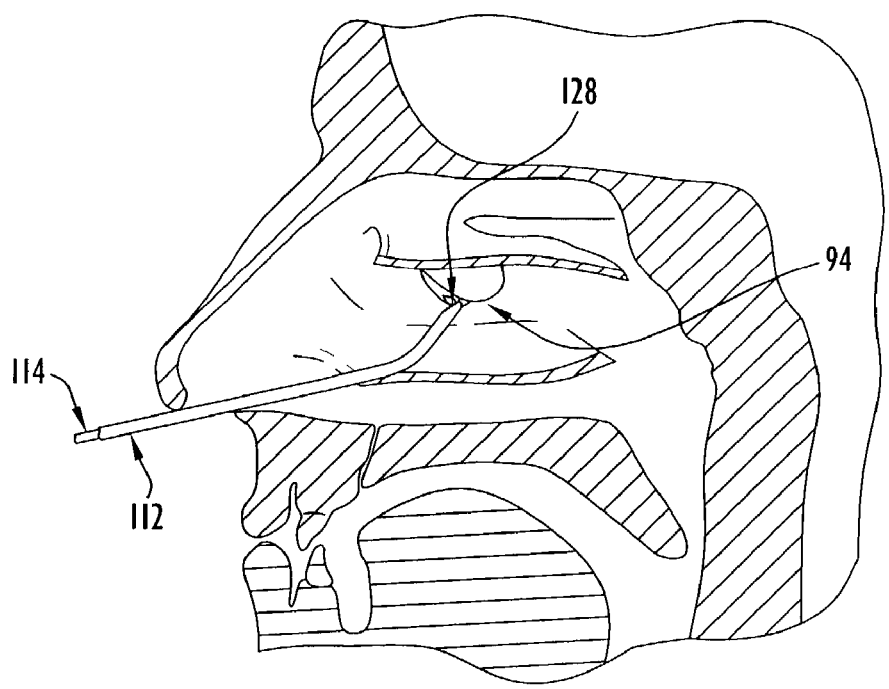
FIG. 18 depicts removal of sinus tissue using the angled tissue cutting instrument of FIG. 13 during a sinus procedure.
Figure 19:
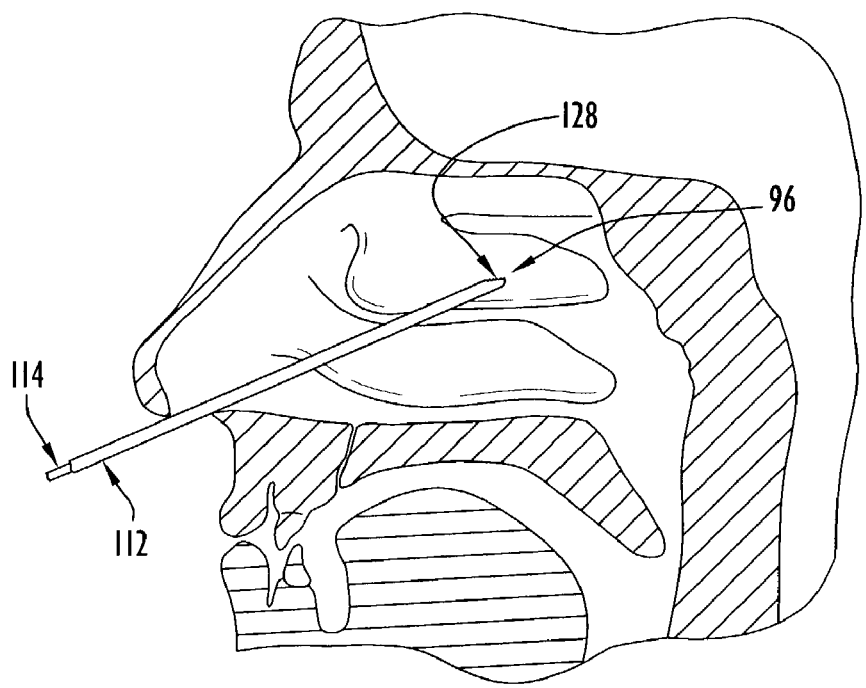
FIG. 19 shows the straightened tissue cutting instrument obtained by straightening the angled tissue cutting instrument of FIG. 13 subsequent to removal of sinus tissue therewith and used to further remove sinus tissue during the sinus procedure.

FIGS. 18 and 19 depict a surgical procedure including a sinus procedure performed using a tissue cutting instrument system or apparatus comprising angled tissue cutting instrument or sinus blade 110 and straightening tool 50. As shown in FIG. 18, the angled tissue cutting instrument 110 is introduced in a patient's nostril to position the opening 128 of outer member 112 adjacent anatomical tissue to be removed in the sinus. As an example, the opening 128 is shown positioned in the maxillary sinus 94, access to which is facilitated by the angled configuration of the blade. The inner member 114 is rotated within the outer member 112 via the powered surgical handpiece 84, and the cutting edges 144 and 146 are used to remove anatomical tissue of the maxillary sinus. Suction or aspiration is accomplished through the inner member 114 as described above for angled tissue cutting instrument 110. The angled tissue cutting instrument 110 is then removed from the patient's nostril and is inserted in the straightening tool 50 as described above in connection with FIGS. 14 and 15. The proximal length portion 118 of outer member 112 extending externally from the positioning block 54 is moved, pivoted or rotated as described and shown for FIG. 16 to obtain a longitudinally or axially straightened outer member 112 as described and shown for FIG. 17. The thusly straightened tissue cutting instrument 110 is inserted in the patient's nostril as depicted in FIG. 19, and the inner member 114 is rotated within the outer member 112 to remove additional sinus tissue 96 in the sinus with the cutting edges 144 and 146. When tissue removal using the straightened tissue cutting instrument 110 is complete, the instrument 110 is removed from the nostril.

Figure 20:
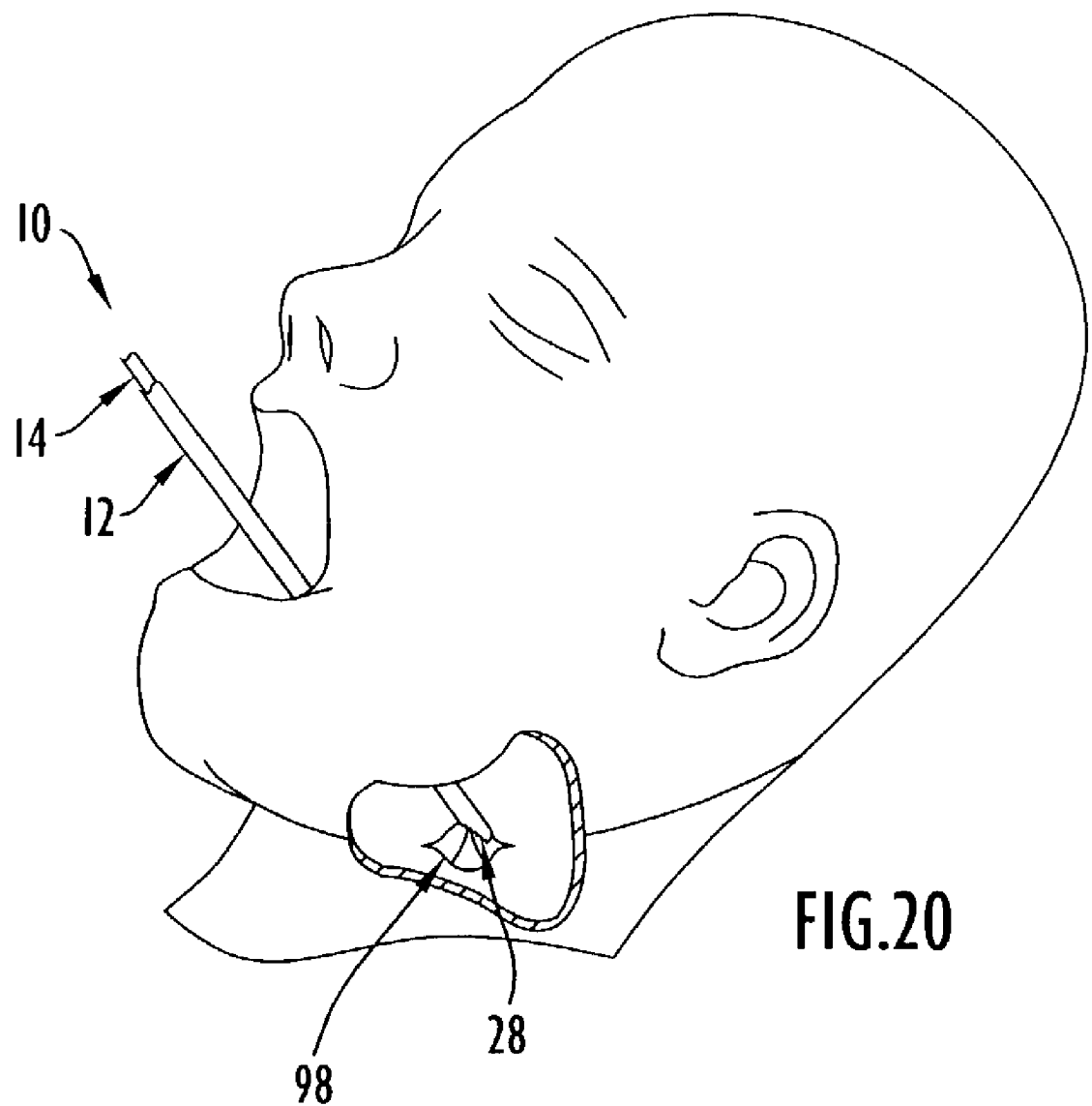
FIG. 20 depicts a longitudinally straightened tissue cutting instrument obtained by straightening an angled tissue cutting instrument having a bend pre-formed therein as part of the manufacture or fabrication process and straightened for use in a surgical procedure for tissue removal.

FIG. 20 is representative of a surgical procedure in which an angled tissue cutting instrument having a bend pre- formed therein as part of the manufacture or fabrication process is straightened for use in a surgical procedure as a longitudinally straightened tissue cutting instrument. FIG. 20 depicts angled tissue cutting instrument 10 subsequent to being straightened as described above for FIGS. 6–10. The angled tissue cutting instrument 10 may be provided as a laryngeal blade having an outer member 12 with a pre-formed angle A of about 18 degrees as represented by the Tricut™ Angle-Tip blade and the Skimmer Angle-Tip blade of Medtronic Xomed Surgical Products, which are advantageous for use in supraglottic and subglottic papilloma removal or debulking, tumor debulking, tracheal stenosis and trans-sphenoidal hypophysectomy. The angled tissue cutting instrument 10 may be longitudinally straightened by the surgeon in the operating room or may be straightened by qualified personnel prior to arrival in the operating room. Once the angled tissue cutting instrument 10 has been straightened as explained above, the resulting longitudinally straightened tissue cutting instrument 10 is used in a surgical procedure to remove anatomical tissue. FIG. 20 shows the distal end of the longitudinally straightened tissue cutting instrument 10 introduced through the patient's mouth to position the opening 28 in outer member 12 adjacent to and facing laryngeal tissue 98, such as tissue of the glottis, that is to be removed. The inner member 14 is rotated within the outer member 12, and the cutting edges of the inner and outer members cut the laryngeal tissue. Of course, anatomical debris may be removed by suction or aspiration through the straightened tissue cutting instrument. When tissue removal using the straightened tissue cutting instrument is complete, the instrument 10 is removed from the patient's mouth.

In accordance with the present invention, various types of angled tissue cutting instruments can be straightened including rotary tissue cutting instruments as shown herein as well as oscillatory and reciprocatory tissue cutting instruments with or without an aspiration passage and with or without an irrigation passage. The same straightening tool can be used to straighten angled tissue cutting instruments having different angles, bends or curves at different locations, or the straightening tool can be customized for particular instruments. The straightening tool ensures that the straightened outer member is either completely longitudinally or axially straight or substantially completely longitudinally or axially straight with only a slight positive bend, curve or angle in the direction of the original pre-formed bend. Angled tissue cutting instruments may be straightened using a minimal number of simple procedural steps capable of being performed by one person without extraneous equipment and in a brief amount of time. The ease and rapidity with which angled tissue cutting instruments can be straightened may make it more desirable and advantageous to straighten an angled tissue cutting instrument during a surgical procedure for further use in the surgical procedure as a longitudinally straightened tissue cutting instrument rather than switching from an angled tissue cutting instrument to another different longitudinally straight tissue cutting instrument. The outer members of the angled tissue cutting instruments can be straightened with the inner members withdrawn therefrom, the inner members disposed therein and with or without the powered surgical handpiece coupled with the inner and outer members. The opening in the outer member and the cutting edge, where provided in the outer member, face upwardly or downwardly in the cavity and are protected against damage. The opening and/or cutting edge of the inner member is also protected where the inner member remains within the outer member during straightening. The downwardly facing opening and/or cutting edge of the outer member does not incur any force during straightening since the proximal length portion of the outer member is pivoted downwardly. The upwardly facing opening and/or cutting edge of the outer member also does not incur any force during straightening since the cavity is open. Proper positioning of the outer member in the straightening tool is easily accomplished by abutment of the outer member distal end with the rearward wall. Proper positioning of the outer member in the straightening tool can be confirmed tactilely and can also be confirmed visually due to the cavity being open. Straightening of the outer member is effected without kinking and/or misalignments with the powered surgical handpiece. Straightening of the outer member is controlled via abutment of the proximal length portion with the floor of the slot such that trial and error adjustments are not necessary. The straightening tool is sterilizable for repeated use or may be disposable for single patient use. The straightening tool is without moving parts and small recesses such that the effectiveness and reliability of sterilization is enhanced. Surgical procedures in which it is desirable to employ both angled and straight tissue cutting instruments are facilitated. Use of the most optimal blade configurations as well as the most optimal distal end cutting configurations for tissue removal during a surgical procedure is promoted. The cost and time for surgical procedures and the required number of tissue cutting instruments for surgical procedures may all be reduced. The straightening tool is particularly advantageous for use in T&A procedures, sinus procedures and laryngeal procedures but may be used to straighten angled tissue cutting instruments in other surgical procedures. In the methods of the present invention, suction and/or irrigation may be accomplished via the tissue cutting instruments.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A straightening tool for straightening an angled tissue cutting instrument including an elongate outer tubular member having a proximal length portion and an initial bend connecting the proximal length portion to a distal length portion extending from the bend to a distal end, and an elongate, flexible inner member movably disposed within the outer member to cut anatomical tissue, said straightening tool comprising
a body having a central longitudinal axis, an elongate handle and an elongate positioning block extending longitudinally, forwardly from said handle, said handle and said positioning block being coaxial with said central longitudinal axis, said positioning block having a cavity defined between an internal rearward wall of said positioning block and an internal rearward intermediate wall of said positioning block spaced forwardly from said rearward wall, said cavity having a bottom wall connecting said rearward wall and said rearward intermediate wall, said cavity being open along a top of said positioning block, said positioning block having a longitudinal slot extending from an internal forward intermediate wall of said positioning block to a forward end wall of said positioning block, said slot being bounded rearwardly by said forward intermediate wall, inferiorly by a floor and laterally by opposing lateral walls, said slot having a top opening along said top of said positioning block and a forward opening along said forward end wall, said top opening communicating with said forward opening at said forward end wall, said positioning block having an internal bore extending longitudinally between said rearward intermediate wall and said forward intermediate wall, said bore being coaxial with said central longitudinal axis and having a rearward opening along said rearward intermediate wall communicating with said cavity adjacent said bottom wall and a forward opening along said forward intermediate wall communicating with said slot adjacent said floor, said floor extending angularly, downwardly from said bore to said forward opening at an angle, said bore having a cross-sectional dimension for receiving the distal length portion of the outer member therethrough to position the distal end of the outer member in abutment with said rearward wall and to position the bend in said slot with the proximal length portion extending externally from said top opening, said bore confining the distal length portion against radial movement to permit the proximal length portion to be pivoted into abutment with said floor of said slot to effect straightening of the outer member.

2. The straightening tool recited in claim 1 wherein said handle comprises a cylindrical section terminating rearwardly at a rearward end and forwardly at a neck tapering from said cylindrical section to said positioning block.

3. The straightening tool recited in claim 2 wherein said cylindrical section has an external diameter and said neck has a truncated conical configuration with a taper of about 45 degrees relative to said external diameter of said cylindrical section.

4. The straightening tool recited in claim 1 wherein said rearward wall and said rearward intermediate wall are planar and parallel to one another in a direction perpendicular to said central longitudinal axis.

5. The straightening tool recited in claim 4 wherein said bottom wall of said cavity is planar and perpendicular to said rearward wall and said rearward intermediate wall.

6. The straightening tool recited in claim 5 wherein said positioning block has a cylindrical external configuration and said cavity is open along an opening extending arcuately along said cylindrical external configuration.

7. The straightening tool recited in claim 6 wherein said opening of said cavity extends arcuately along said top and along opposing sides of said positioning block.

8. The straightening tool recited in claim 1 wherein said cavity is open along said top and along opposing sides of said positioning block.

9. The straightening tool recited in claim 1 wherein said angle is in the range of 5 to 7 degrees.

10. The straightening tool recited in claim 9 wherein said angle is 5 degrees.

11. The straightening tool recited in claim 1 wherein said body is integrally, unitarily formed as one piece.

12. A straightening tool for straightening an angled tissue cutting instrument including an elongate outer tubular member having a proximal length portion and an initial bend connecting the proximal length portion to a distal length portion extending from the bend to a distal end, and an elongate, flexible inner member movably disposed within the outer member to cut anatomical tissue, said straightening tool comprising
a body having a central longitudinal axis, an elongate handle and an elongate positioning block extending longitudinally, forwardly from said handle to a forward end wall of said positioning block, said handle and said positioning block being coaxial with said central longitudinal axis, a cavity in said positioning block bounded rearwardly by an internal rearward wall of said positioning block, forwardly by an internal rearward intermediate wall of said positioning block and inferiorly by an internal, planar bottom wall of said positioning block, an internal bore in said positioning block extending from an opening on said rearward intermediate wall to an opening on an internal forward intermediate wall of said positioning block, said bore being coaxial with said central longitudinal axis and being tangential to a plane containing said bottom wall, said positioning block having a slot extending longitudinally from said forward intermediate wall to said forward end wall, said slot having a top opening along a top of said positioning block and a forward opening along said forward end wall, said slot having a floor extending angularly, downwardly at an angle from said opening on said forward intermediate wall to said forward end wall, said bore being adapted to receive the distal length portion of the outer member therethrough to position the distal end of the outer member in abutment with said rearward wall and to position the bend within said slot with the proximal length portion extending externally from said top opening of said slot, said bore being adapted to confine the distal length portion against movement in a radial direction to permit the proximal length portion to be pivoted into abutment with said floor to effect straightening of the outer member.

13. The straightening tool recited in claim 12 wherein said angle is in the range of five to seven degrees defined between said floor and said plane.

14. The straightening tool recited in claim 13 wherein said angle is five degrees.

15. The straightening tool recited in claim 13 wherein said floor has a partial cylindrical configuration and said angle is defined between said plane and a plane tangential to said partial cylindrical configuration.

16. The straightening tool recited in claim 12 wherein said handle has an external cylindrical configuration and said positioning block has an external cylindrical configuration smaller than said external cylindrical configuration of said handle.

17. The straightening tool recited in claim 12 wherein said planar bottom wall is parallel to said central longitudinal axis and said rearward wall and said rearward intermediate wall are perpendicular to said bottom wall.

18. The straightening tool recited in claim 12 wherein said bore is cylindrical and has a radius, and said floor is curved with a radius of curvature the same as said radius of said bore.

19. The straightening tool recited in claim 18 wherein said bore is adapted to received the outer member with a close fit.

20. The straightening tool recited in claim 12 wherein said forward end wall is planar.

21. The straightening tool recited in claim 12 wherein said slot includes opposing side walls extending upwardly from said floor to said top opening of said slot.

22. The straightening tool recited in claim 21 wherein said side walls are planar and parallel.

23. The straightening tool recited in claim 21 wherein said slot has a curved rearward end along said forward intermediate wall.

24. The straightening tool recited in claim 12 wherein said straightening tool is sterilizable for repeated use.

25. The straightening tool recited in claim 12 wherein said straightening tool is disposable for single patient use.

26. A tissue cutting instrument system for use in surgery comprising
an angled tissue cutting instrument comprising an elongate outer tubular member and an elongate inner member movably received within said outer member, said outer member having a proximal length portion and an initial bend connecting said proximal length portion to a distal length portion, said distal length portion extending from said bend to a distal end having an opening, said inner member being flexible to conform to said bend and having a cutting edge exposed by said opening to cut anatomical tissue when said inner member is moved within said outer member; and
a straightening tool comprising a central longitudinal axis, a handle and a positioning block extending from said handle to a forward end wall, said positioning block having an internal bore therein coaxial with said central longitudinal axis, said bore being disposed between and communicating with a cavity of said positioning block and a slot of said positioning block, said cavity extending longitudinally, rearwardly from said bore to a rearward internal wall of said positioning block, said slot extending longitudinally, forwardly from said bore to a forward opening along said forward end wall, said slot having a floor extending from said bore to said forward opening at a downward angle, said slot having opposing side walls and a top opening along a top of said positioning block, said forward opening communicating with said top opening at said forward end wall, said outer member being insertable in said straightening tool with said distal length portion extending through said bore to position said distal end in abutment with said rearward wall and said bend in said slot with said proximal length portion extending externally from said top opening, said bore confining said distal length portion against movement in a direction radial to said central longitudinal axis to permit said proximal length portion to be moved downwardly in said slot and into abutment with said floor to effect straightening of said outer tubular member whereby said outer member and said inner member form a longitudinally straightened tissue cutting instrument.

27. The tissue cutting instrument system recited in claim 26 wherein said proximal length portion has a central longitudinal axis and said bend has a configuration establishing an angle of about 40 degrees between a central longitudinal axis of said distal length portion and said central longitudinal axis of said proximal length portion.

28. The tissue cutting instrument system recited in claim 27 wherein said bend has a radius of curvature of about 0.0875 inch.

29. The tissue cutting instrument system recited in claim 28 wherein said bend is located about 0.7 inch from said distal end.

30. The tissue cutting instrument system recited in claim 26 wherein said proximal length portion has a central longitudinal axis and said bend has a configuration establishing an angle of about 60 degrees between a central longitudinal axis of said distal length portion and said central longitudinal axis of said proximal length portion.

31. The tissue cutting instrument system recited in claim 26 wherein said angled tissue cutting instrument is a RADenoid® Blade of Medtronic Xomed Surgical Products.

32. The tissue cutting instrument system recited in claim 26 wherein said angled tissue cutting instrument is a Rad 40® Curved Blade of Medtronic Xomed Surgical Products.

33. The tissue cutting instrument system recited in claim 26 wherein said angled tissue cutting instrument is a laryngeal blade.

34. The tissue cutting instrument system recited in claim 26 wherein said angled tissue cutting instrument is a Rad 60 X-TREME™ Curved Blade of Medtronic Surgical Products.

35. The tissue cutting instrument system recited in claim 26 wherein said outer member includes a cutting edge along said opening in said outer member cooperable with said cutting edge of said inner member to cut anatomical tissue.

36. The tissue cutting instrument system recited in claim 26 wherein said inner member is tubular, said cutting edge is disposed at a distal end of said inner member and further including a suction port at said distal end of said inner member for aspirating anatomical debris through said inner member.

37. The tissue cutting instrument system recited in claim 26 wherein said inner member is rotatably disposed within said outer member.

38. The tissue cutting instrument system recited in claim 37 wherein said outer member includes a proximal end connected to an outer member hub, said inner member includes a proximal end connected to an inner member hub, and said hubs are adapted to be releasably coupled with a powered surgical handpiece by which said inner member is rotated relative to and within said outer member.

39. The tissue cutting instrument system recited in claim 37 wherein said inner member has a flexible length region disposed adjacent said bend by with said inner member conforms to said bend while being rotated within said outer member.

40. The tissue cutting instrument system recited in claim 26 wherein said distal length portion is longitudinally straight and said proximal length portion is longitudinally straight.

41. The tissue cutting instrument system recited in claim 26 wherein said tissue cutting instrument includes an irrigation channel.

42. The tissue cutting instrument system recited in claim 26 wherein said cavity has a dimension to accommodate said opening of said outer member.

43. A method of performing surgery comprising the steps of
introducing a distal end of an angled tissue cutting instrument at an operative site in a patient's body, the tissue cutting instrument having an elongate outer tubular member with a proximal length portion and an initial bend connecting the proximal length portion to a distal length portion extending from the bend to a distal end having an opening, and an elongate inner member disposed within the outer member and having a cutting edge exposed by the opening;
positioning the cutting edge adjacent anatomical tissue to be removed;
moving the inner member within the outer member to cut the anatomical tissue with the cutting edge;
withdrawing the angled tissue cutting instrument from the patient's body;
inserting the outer member through a longitudinal bore of a straightening tool until the distal end abuts an abutment wall of the straightening tool with the distal length portion disposed within the bore in coaxial alignment with the straightening tool, the bend disposed in a slot of the straightening tool and the proximal length portion extending externally from an opening of the slot;
applying manual pressure to the proximal length portion to pivot the proximal length portion within the slot in a direction opposite the initial bend until the proximal length portion is in abutment with a floor of the slot extending from the bore at an angle in the direction opposite the initial bend;
releasing the manual pressure on the proximal length portion so that the proximal length portion may spring back in the direction of the initial bend to obtain a longitudinally straightened outer member;
removing the straightened outer member from the straightening tool;
introducing the distal end of the straightened outer member at an operative site in the patient's body with the inner member received therein to form a longitudinally straightened tissue cutting instrument;
positioning the cutting edge adjacent anatomical tissue to be removed;
moving the inner member within the straightened outer member to cut the anatomical tissue with the cutting edge; and
withdrawing the straightened tissue cutting instrument from the patient's body.

44. The method of performing surgery recited in claim 43 wherein said steps of moving include rotating the inner member within the outer member.

45. The method of performing surgery recited in claim 43 and further including, simultaneous with at least one of said steps of moving, the step of aspirating anatomical debris from the operative site through the tissue cutting instrument.

46. The method of performing surgery recited in claim 45 wherein said step of aspirating includes aspirating anatomical debris through the inner member.

47. The method of performing surgery recited in claim 43 and further including, prior to at least one of said steps of withdrawing, the step of supplying irrigating fluid at the operative site along the tissue cutting instrument.

48. The method of performing surgery recited in claim 43 wherein said step of applying manual pressure includes pivoting the proximal length portion from the bore at an angle of five to seven degrees in the direction opposite the initial bend.

49. The method of performing surgery recited in claim 48 wherein said step of pivoting includes pivoting the proximal length portion downwardly at an angle of five degrees in the direction opposite the initial bend.

50. The method of performing surgery recited in claim 43 wherein said step of releasing includes obtaining a completely longitudinally straight outer member.

51. The method of performing surgery recited in claim 43 wherein said step of releasing includes obtaining a substantially completely longitudinally straight outer member in which the outer member has a slight bend in the same direction as the initial bend.

52. The method of performing surgery recited in claim 43 wherein said step of inserting includes inserting the outer member in the straightening tool with the inner member disposed within the outer member.

53. The method of performing surgery recited in claim 52 wherein said step of inserting includes inserting the outer member in the straightening tool with the outer and inner members coupled with a powered surgical handpiece.

54. A method of performing a combined tonsillectomy and adenoidectomy procedure comprising the steps of
introducing a distal end of an angled tissue cutting instrument in the nasopharynx of a patient's body, the tissue cutting instrument having an elongate outer tubular member with a proximal length portion and an initial bend connecting the proximal length portion to a distal length portion extending from the bend to a distal end having an opening, and an elongate inner member disposed within the outer member and having a cutting edge exposed by the opening;

positioning the cutting edge adjacent an adenoid;

moving the inner member within the outer member to cut tissue of the adenoid with the cutting edge;

withdrawing the angled tissue cutting instrument from the patient's body;

inserting the outer member in a longitudinal bore of a straightening tool such that the distal length portion is confined against radial movement with the bend disposed in a slot of the straightening tool and the proximal length portion extending externally from an opening of the slot;

applying manual pressure to the proximal length portion to pivot the proximal length portion within the slot in a direction opposite the initial bend until the proximal length portion is in abutment with a floor of the slot extending from the bore at an angle in the direction opposite the initial bend;

releasing the manual pressure on the proximal length portion so that the proximal length portion may spring back in the direction of the initial bend to obtain a longitudinally straightened outer member;

removing the straightened outer member from the straightening tool;

introducing the distal end of the straightened outer member in the patient's body with the inner member received therein to form a longitudinally straightened tissue cutting instrument;

positioning the cutting edge adjacent a tonsil;

moving the inner member within the straightened outer member to cut tonsular tissue of the tonsil with the cutting edge; and withdrawing the longitudinally straightened tissue cutting instrument from the patient's body.

55. A method of performing sinus surgery comprising the steps of introducing a distal end of an angled tissue cutting instrument in a sinus cavity in a patient's body, the tissue cutting instrument having an elongate outer tubular member with a proximal length portion and an initial bend connecting the proximal length portion to a distal length portion extending from the bend to a distal end having an opening, and an elongate inner member disposed within the outer member and having a cutting edge exposed by the opening;

positioning the opening adjacent sinus tissue to be removed;

moving the inner member within the outer member to cut the sinus tissue with the cutting edge;

withdrawing the angled tissue cutting instrument from the patient's body;

inserting the outer member in a longitudinal bore of a straightening tool such that the distal length portion is confined against radial movement with the bend disposed in a slot of the straightening tool and the proximal length portion extending externally from a top opening of the slot;

applying manual pressure to the proximal length portion to pivot the proximal length portion within the slot in a direction opposite the initial bend until the proximal length portion is in abutment with a floor of the slot extending from the bore at an angle in the direction opposite the initial bend;

releasing the manual pressure on the proximal length portion so that the proximal length portion may spring back in the direction of the initial bend to obtain a longitudinally straightened outer member;

removing the straightened outer member from the straightening tool;

introducing the distal end of the straightened outer member in the sinus cavity with the inner member received therein to form a longitudinally straightened tissue cutting instrument;

positioning the cutting edge adjacent sinus tissue to be removed;

moving the inner member within the straightened outer member to cut the sinus tissue with the cutting edge; and withdrawing the longitudinally straightened tissue cutting instrument from the patient's body.

56. A method of performing surgery comprising the steps of selecting an angled tissue cutting instrument having an elongate outer tubular member manufactured with a pre-formed bend connecting a proximal length portion of the outer member to a distal length portion of the outer member extending from the bend to a distal end having an opening, and an elongate inner member disposed within the outer member and having a cutting edge exposed by the opening;

inserting the outer member through a longitudinal bore of a straightening tool until the distal end abuts an abutment wall of the straightening tool with the distal length portion disposed within the bore in coaxial alignment with the straightening tool, the bend disposed in a slot of the straightening tool and the proximal length portion extending externally from an opening of the slot;

applying manual pressure to the proximal length portion to pivot the proximal length portion within the slot in a direction opposite the bend until the proximal length portion is in abutment with a floor of the slot extending from the bore at an angle in the direction opposite the bend;

releasing the manual pressure on the proximal length portion so that the proximal length portion may spring back in the direction of the original bend to obtain a longitudinally straightened outer member;

removing the straightened outer member from the straightening tool;

introducing the distal end of the straightened outer member at an operative site in the patient's body with the inner member received therein to form a longitudinally straightened tissue cutting instrument;

positioning the cutting edge adjacent anatomical tissue to be removed;

moving the inner member within the straightened outer member to cut the anatomical tissue with the cutting edge; and withdrawing the straightened tissue cutting instrument from the patient's body.

57. A tissue cutting instrument system for use in surgery comprising an angled tissue cutting instrument comprising an elongate outer tubular member and an elongate inner member movably received within said outer member, said outer member having a proximal length portion and an initial bend connecting said proximal length portion to a distal length portion, said distal length portion extending from said initial bend to a distal end having an opening, said inner member including a flexible region conforming to said bend and a cutting edge exposed by said opening to cut anatomical tissue when said inner member is moved within said outer member; and a straightening tool comprising a handle, a positioning block attached to said handle, a confinement passage in said positioning block for receiving said distal length portion, and a contact surface in said positioning block extending from said confinement passage at an angle, said outer member being insertable in said straightening tool with said distal length portion disposed in said confinement passage and said initial bend disposed externally of said confinement passage with said proximal length portion extending externally from said positioning block in a direction opposite said contact surface, said confinement passage confining said distal length portion against movement in a direction radial to a central longitudinal axis of said distal length portion while permitting said proximal length portion to be pivoted into contact with said contact surface, said angle of said contact surface being selected to impart a reverse bend in said outer member, opposite said initial bend, when said proximal length portion is in contact with said contact surface and to straighten said outer member after spring back movement of said proximal length portion away from said contact surface in the direction of said initial bend, whereby said outer member and said inner member form a longitudinally straightened tissue cutting instrument.

58. A method of performing surgery comprising the steps of introducing a distal end of an angled tissue cutting instrument at an operative site in a patient's body, the tissue cutting instrument having an elongate outer tubular member with a proximal length portion and an initial bend connecting the proximal length portion to a distal length portion extending from the initial bend to a distal end having an opening, and an elongate inner member movably disposed within the outer member and having a cutting edge exposed by the opening;

positioning the cutting edge adjacent anatomical tissue to be removed;

moving the inner member within the outer member to cut the anatomical tissue with the cutting edge;

withdrawing the angled tissue cutting instrument from the patient's body;

inserting the distal length portion in a confinement passage of a straightening tool to confine the distal length portion within the confinement passage;

applying manual pressure to the proximal length portion, in a direction opposite the initial bend and relative to the distal length portion confined in the confinement passage, until the proximal length portion is reverse bent into abutment with a contact surface of the positioning block extending from the confinement passage at an angle in the direction opposite the initial bend;

releasing the manual pressure on the proximal length portion so that the proximal length portion springs back in the direction of the initial bend to obtain a longitudinally straightened outer member;

removing the straightened outer member from the straightening tool;

introducing the distal end of the straightened outer member at an operative site in the patient's body with the inner member received therein to form a longitudinally straightened tissue cutting instrument;

positioning the cutting edge adjacent anatomical tissue to be removed;

moving the inner member within the straightened outer member to cut the anatomical tissue with the cutting edge; and withdrawing the straightened tissue cutting instrument from the patient's body.

* * * * *